US012558522B2

(12) United States Patent
Chu

(10) Patent No.: US 12,558,522 B2
(45) Date of Patent: Feb. 24, 2026

(54) FORCE GAUGE AND METHOD OF USE

(71) Applicant: BOSTON SCIENTIFIC SCIMED, INC., Maple Grove, MN (US)

(72) Inventor: Michael S H Chu, Brookline, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 218 days.

(21) Appl. No.: 18/121,450

(22) Filed: Mar. 14, 2023

(65) Prior Publication Data

US 2023/0218868 A1    Jul. 13, 2023

Related U.S. Application Data

(63) Continuation of application No. 16/136,053, filed on Sep. 19, 2018, now Pat. No. 11,628,279.

(Continued)

(51) Int. Cl.

| | |
|---|---|
| *A61M 25/06* | (2006.01) |
| *A61B 17/34* | (2006.01) |
| *A61B 90/00* | (2016.01) |
| *A61M 25/00* | (2006.01) |
| *A61M 29/02* | (2006.01) |

(52) U.S. Cl.
CPC ..... *A61M 25/0662* (2013.01); *A61B 17/3421* (2013.01); *A61B 17/3472* (2013.01); *A61M 25/0074* (2013.01); *A61M 29/02* (2013.01); *A61B 2017/345* (2013.01); *A61B 2090/064* (2016.02); *A61M 25/0017* (2013.01); *A61M 2029/025* (2013.01); *A61M 2205/18* (2013.01); *A61M 2205/332* (2013.01); *A61M 2210/1089* (2013.01)

(58) Field of Classification Search
CPC .... A61B 2017/00336; A61B 2017/345; A61B 2560/0462; A61B 2090/064; A61B 2562/0247; A61M 25/00; A61M 25/0017; A61M 25/0074; A61M 25/0097; A61M 25/0662; A61M 29/00; A61M 29/02; A61M 2025/0002; A61M 2025/0687; A61M 2029/025; A61M 2205/332; A61M 2210/1089
USPC ........................................................ 606/191
See application file for complete search history.

(56) References Cited

U.S. PATENT DOCUMENTS

| | | | |
|---|---|---|---|
| 4,721,507 | A | 1/1988 | Chin |
| 4,820,283 | A | 4/1989 | Schickling |

(Continued)

FOREIGN PATENT DOCUMENTS

| | | |
|---|---|---|
| CN | 106659512 A | 5/2017 |
| GB | 2446447 A | 8/2008 |
| WO | 2015134846 A1 | 9/2015 |

OTHER PUBLICATIONS

International Search Report and Written Opinion for application No. PCT/US2018/051804 dated Jan. 3, 2019, 11 pages.

(Continued)

*Primary Examiner* — Jocelin C Tanner
(74) *Attorney, Agent, or Firm* — Seager, Tufte & Wickhem, LLP

(57) ABSTRACT

The present disclosure relates generally to the field of medical devices and methods to assist in the introduction of an instrument into a patient, and more particularly to medical devices for measuring and/or monitoring forces applied during introduction of an access sheath through a body lumen.

19 Claims, 20 Drawing Sheets

Related U.S. Application Data

(60) Provisional application No. 62/560,887, filed on Sep. 20, 2017.

(56)                    References Cited

U.S. PATENT DOCUMENTS

| | | | |
|---|---|---|---|
| 5,578,053 | A | 11/1996 | Yoon |
| 5,817,104 | A | 10/1998 | Bilitz et al. |
| 6,656,160 | B1 | 12/2003 | Taylor et al. |
| 2009/0030427 | A1 | 1/2009 | Razvi et al. |
| 2009/0306472 | A1* | 12/2009 | Filipi ................ A61B 1/00135 |
| | | | 606/192 |
| 2012/0259203 | A1* | 10/2012 | Devereux ......... A61M 25/0631 |
| | | | 600/106 |
| 2014/0236222 | A1 | 8/2014 | Tegels |
| 2015/0327878 | A1 | 11/2015 | Chu et al. |
| 2016/0199079 | A1 | 7/2016 | Chu et al. |
| 2016/0213860 | A1 | 7/2016 | Racz |
| 2018/0160888 | A1* | 6/2018 | Bunch .................. A61B 1/3132 |
| 2018/0199799 | A1 | 7/2018 | Chu |

OTHER PUBLICATIONS

Hameed et al., "Outcome of Ureteral Distensibility on the success of ureteroscopy: A prospective hospital-based descriptive study," African Journal of Urology, vol. 23, pp. 33-37, 2017.

\* cited by examiner

FORCE GAUGE AND METHOD OF USE

CROSS REFERENCE TO RELATED APPLICATIONS

This application is a continuation of and claims the benefit of the earlier filing date of U.S. patent application Ser. No. 16/136,053, filed Sep. 19, 2018, and claims the benefit of priority under 35 U.S.C. § 119 to U.S. Provisional Patent Application Ser. No. 62/560,887, filed on Sep. 20, 2017, which applications are hereby incorporated by reference herein their entireties and for all purposes.

FIELD

The present disclosure relates generally to the field of medical devices and methods to assist in the introduction of instruments into a patient, and more particularly to medical devices for measuring and/or monitoring forces applied during introduction of an access sheath through a body lumen.

BACKGROUND

Access sheaths, such as the Navigator™ Ureteral Access Sheath (Boston Scientific Corp., Marlborough, MA) are commonly used to aid in the removal of objects from within a patient and/or to prevent damage to walls of a body lumen during an instrument exchange. For example, an access sheath and dilator may be introduced into a patient's ureter prior to performing a flexible ureteroscopy (URS) procedure to remove kidney stones. Perforation of the ureter may occur if excessive force is required to advance the access sheath/dilator through a narrow or otherwise restricted portion of the ureter.

A variety of advantageous medical outcomes may therefore be realized by the devices and/or methods of the present disclosure, which include a force gauge to allow a medical professional to monitor and control the amount of force applied to a ureter during the placement of an access sheath.

SUMMARY

The present disclosure, in its various aspects, provides advantages and improvements in the medical field, generally with respect to the introduction of medical instruments into a lumen, tract, vessel or cavity of a patient, and more particularly with respect to the introduction of an access sheath for removal of obstructions and/or to conduct medical device exchanges.

In one aspect, the present disclosure relates to a medical device comprising an access sheath. A dilator may be disposed within a lumen of the access sheath and a force gauge may be disposed about a proximal portion of the access sheath. The force gauge may include a grip slidably disposed about the access sheath. A spring may be disposed within a lumen of the grip. A cap may be reversibly attached to the access sheath and distal to the spring. At least a portion of the cap may extend into the lumen of the grip. A proximal end of the grip may include a spring abutment surface configured to contact a proximal end of the spring within the lumen of the grip. A proximal end of the cap may include a spring abutment surface configured to contact a distal end of the spring within the lumen of the grip. The grip may be configured to move relative to the cap to change a height of the spring within the lumen of the grip. An initial height of the spring within the lumen of the grip may be equal to a free length of the spring, e.g., the spring may have an initial restoring force of zero. An initial height of the spring within the lumen of the grip may be less than a free length of the spring, e.g., the spring may have an initial restoring force greater than zero. The access sheath may include a surface feature configured to engage a corresponding mating feature of the cap. The surface feature may include a protrusion and the mating feature may include a snap window. The mating feature may include a thread and the surface feature may include a threaded groove to receive the thread. A proximal portion of the cap may include a pin configured to be received within a corresponding pin slot formed within a distal portion of the grip. One or more indicator marks may be disposed along the pin slot. A position of the pin within the pin slot may indicate a restoring force of the spring within the lumen of the grip. The dilator and access sheath may be configured to move between a locked configuration and an unlocked configuration.

In another aspect, the present disclosure relates to a medical device comprising an access sheath. A dilator may be disposed within a lumen of the access sheath and a force gauge may be disposed about a proximal portion of the access sheath. The force gauge may include a grip slidably disposed about the access sheath. A spring may be disposed within a lumen of the grip. A cap may be rotatably attached to the access sheath and distal to the spring. At least a portion of the cap may extend into the lumen of the grip. A proximal end of the grip may include a spring abutment surface configured to contact a proximal end of the spring within the lumen of the grip. A proximal end of the cap may include a spring abutment surface configured to contact a distal end of the spring within the lumen of the grip. The grip may be configured to move relative to the cap to change a height of the spring within the lumen of the grip. An initial height of the spring within the lumen of the grip may be equal to a free length of the spring, e.g., the spring may have an initial restoring force of zero. An initial height of the spring within the lumen of the grip may be less than a free length of the spring, e.g., the spring may have an initial restoring force greater than zero. The access sheath may include a surface feature configured to engage a corresponding mating feature of the grip. The surface feature may include a plurality of ratchet teeth and a ratchet release slot and the mating feature may include a ratchet catch. The ratchet catch may be disposed within the ratchet release slot when the grip is rotated to a first position. The ratchet catch may be disposed over the ratchet teeth when the grip is rotated to a second position.

In yet another aspect, the present disclosure relates to a method of positioning an access device within a ureter, comprising inserting an access device comprising an access sheath, dilator and force gauge into a ureter of a patient, measuring a resistive force when the access sheath and/or dilator encounters an obstruction in the ureter, and determining whether the measured resistive force exceeds a pre-determined maximum force. The method may further include distally advancing the access sheath and dilator beyond the obstruction if the measured resistive force is less than or equal to the pre-determined maximum force. In addition, or alternatively, the method may further include proximally retracting the access sheath and dilator from within the ureter if the measured resistive force exceeds the pre-determined maximum force. The pre-determined maximum force may be determined by tactile feel, an audible alarm, a visual alarm and/or an indicator mark on the access device.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to access devices and methods for advancing access sheaths through the ureter, it should be appreciated that devices and methods according to the present disclosure may be used with other medical devices to navigate through, and/or position such medical devices (e.g., stents, etc.) within a variety of lumens, tracts, vessels and cavities within the body, including, for example, during endoscopy procedures in the GI tract, urogynecological procedures in the reproductive organs, vascular access or other intravenous procedures, etc.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

Figure 1:
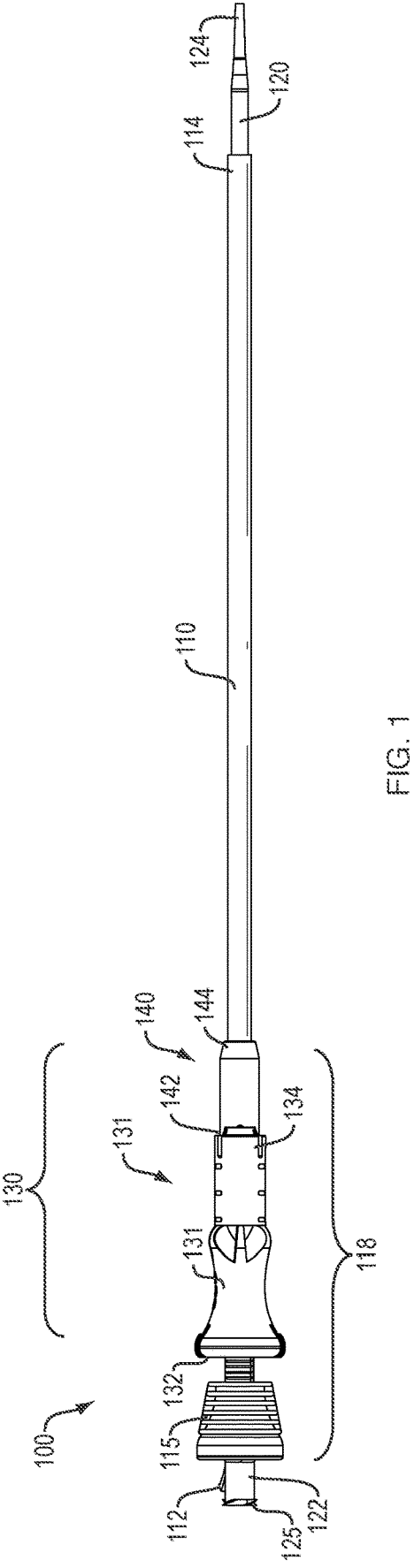
FIG. 1 provides a perspective view of a medical device, according to one embodiment of the present disclosure.
Figure 2A:
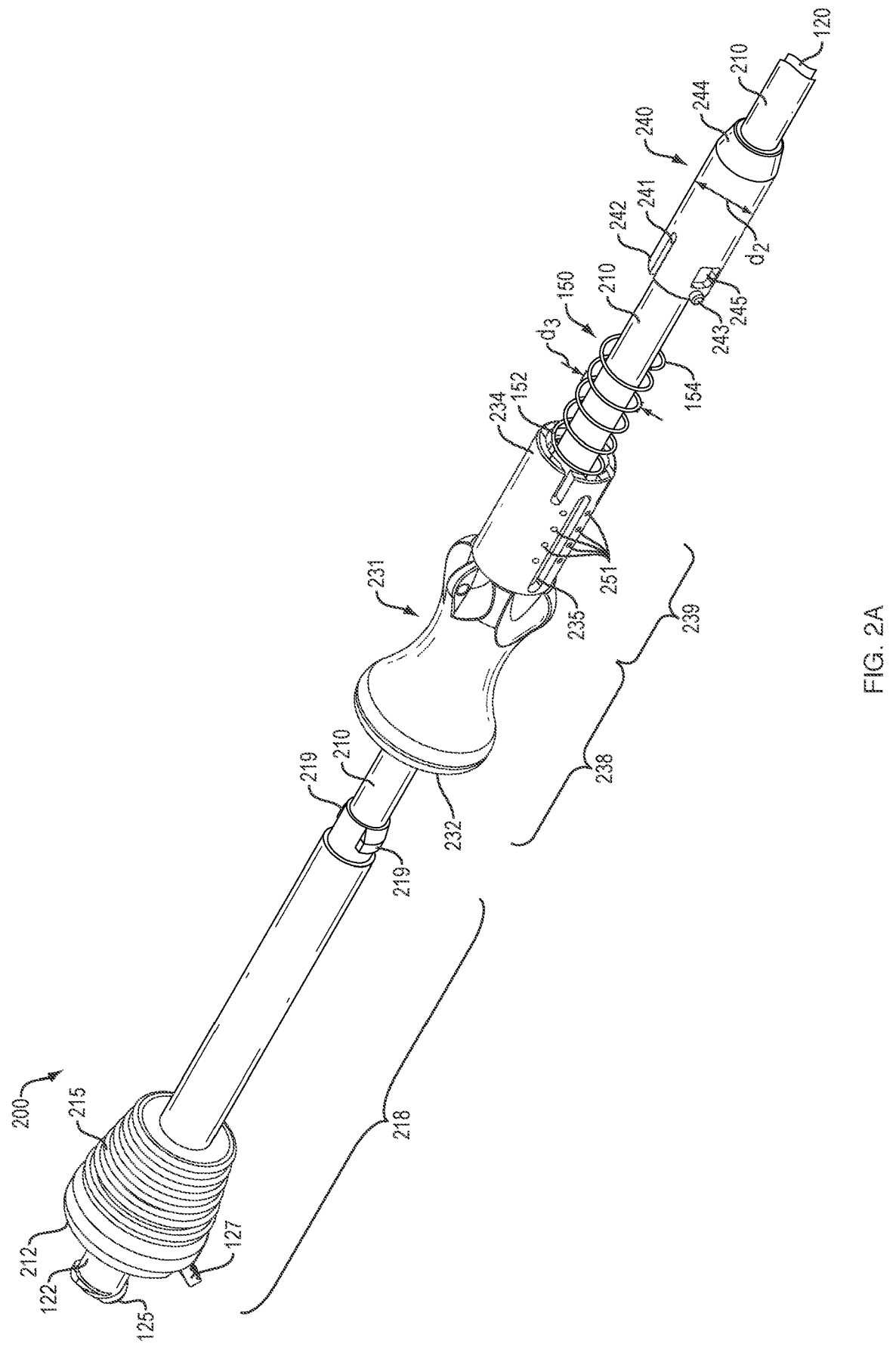
FIGS. 2A-2D provide perspective views of a medical device, according to one embodiment of the present disclosure.
Figure 2B:
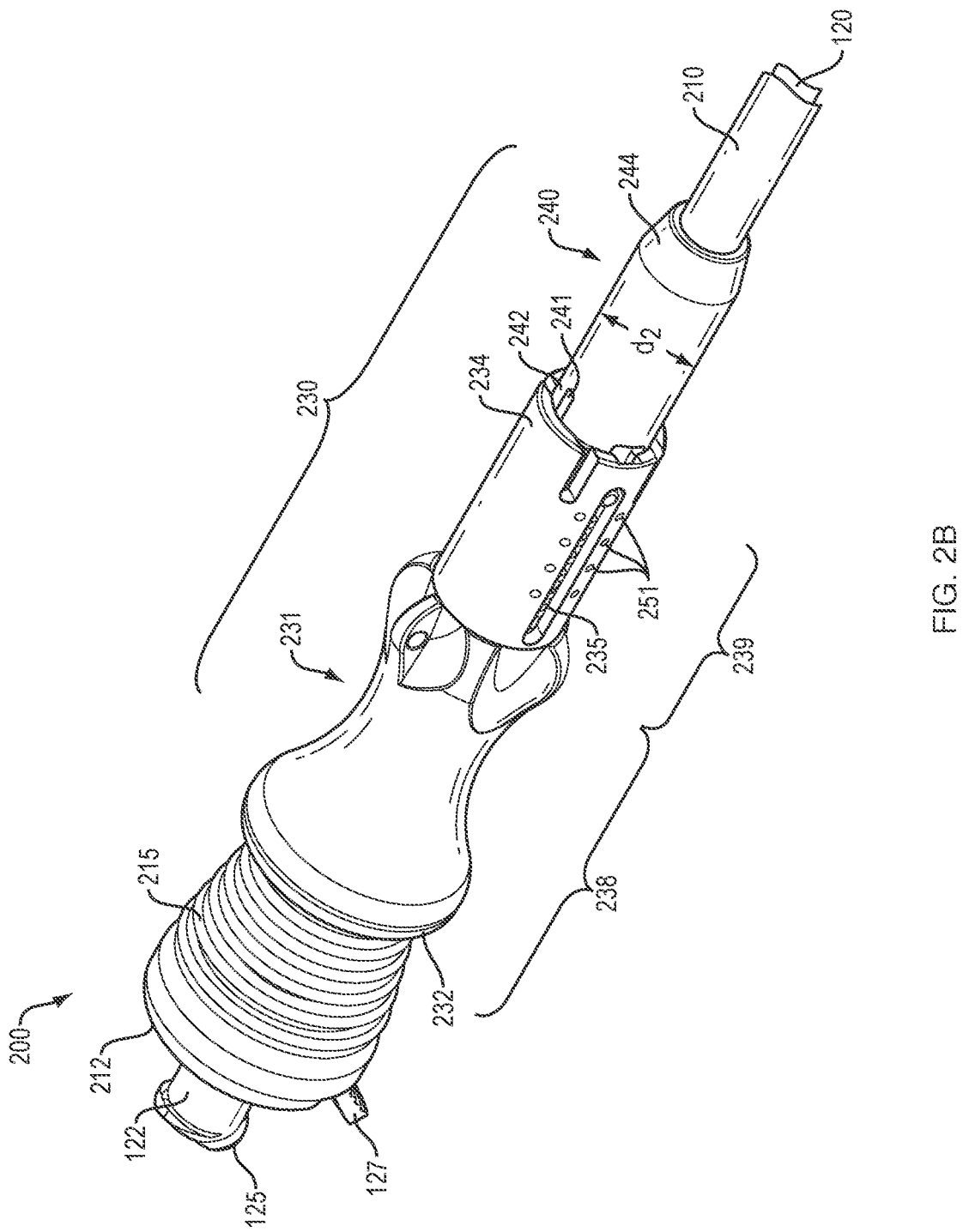
Figure 2C:
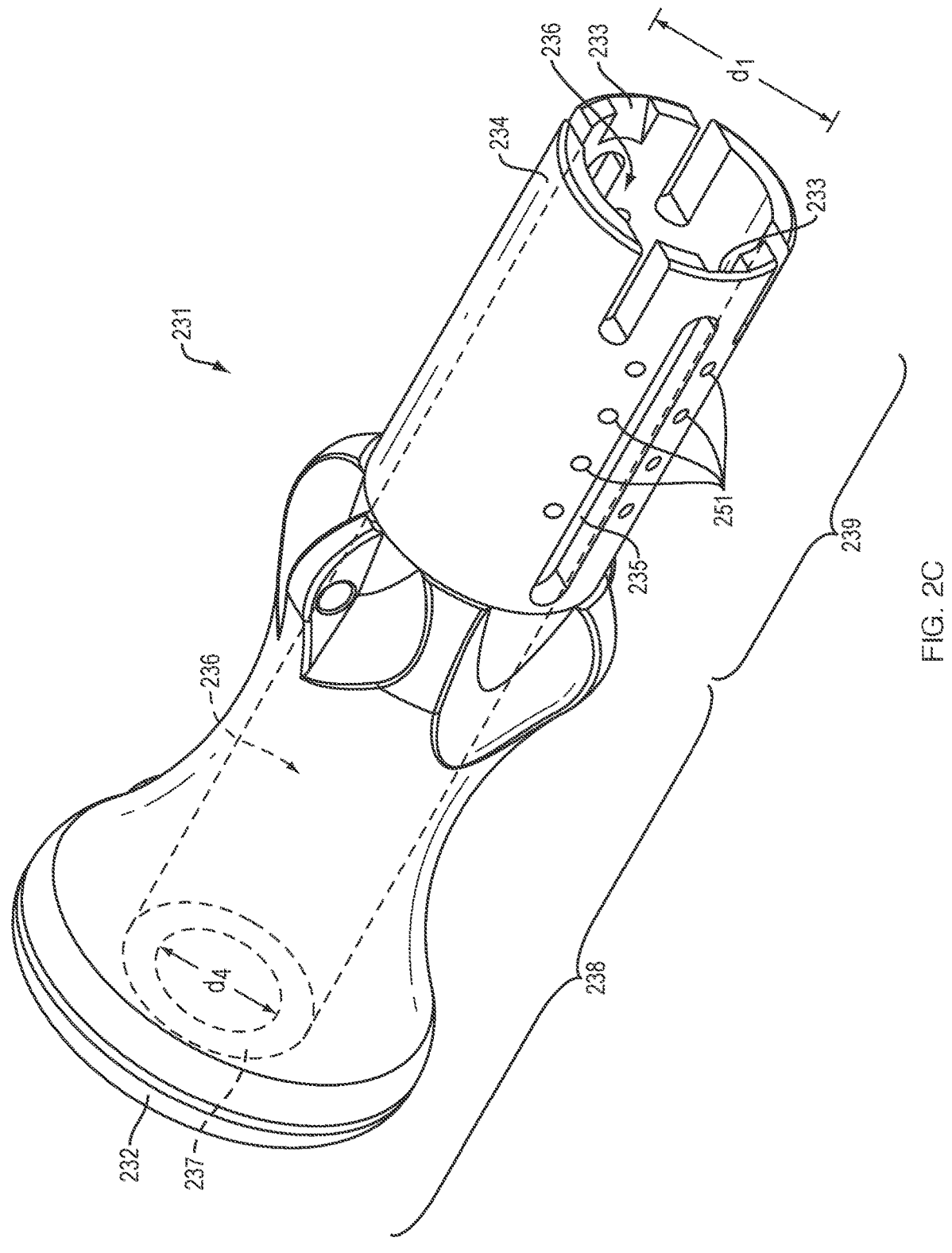
Figure 2D:
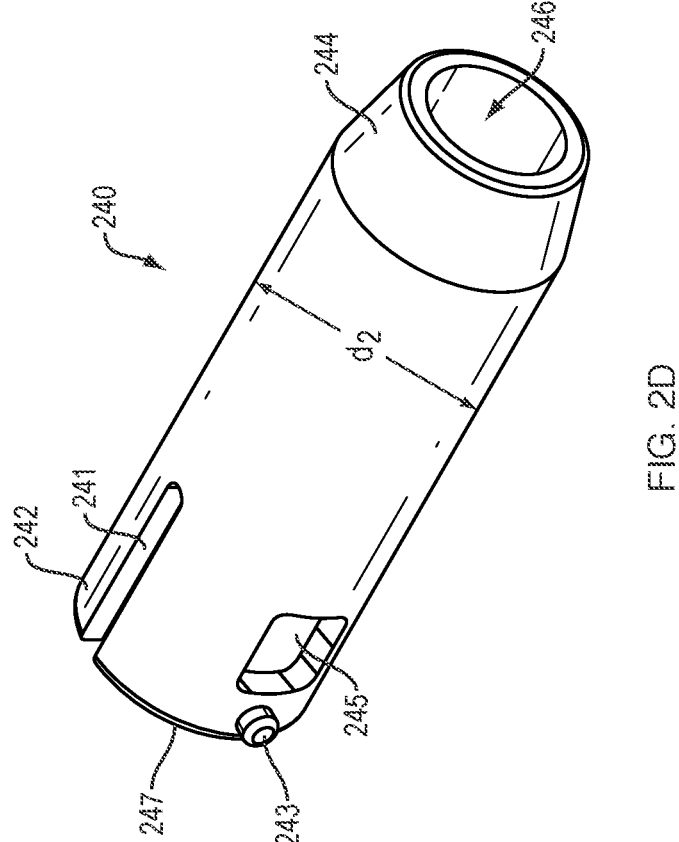
Figure 3A:
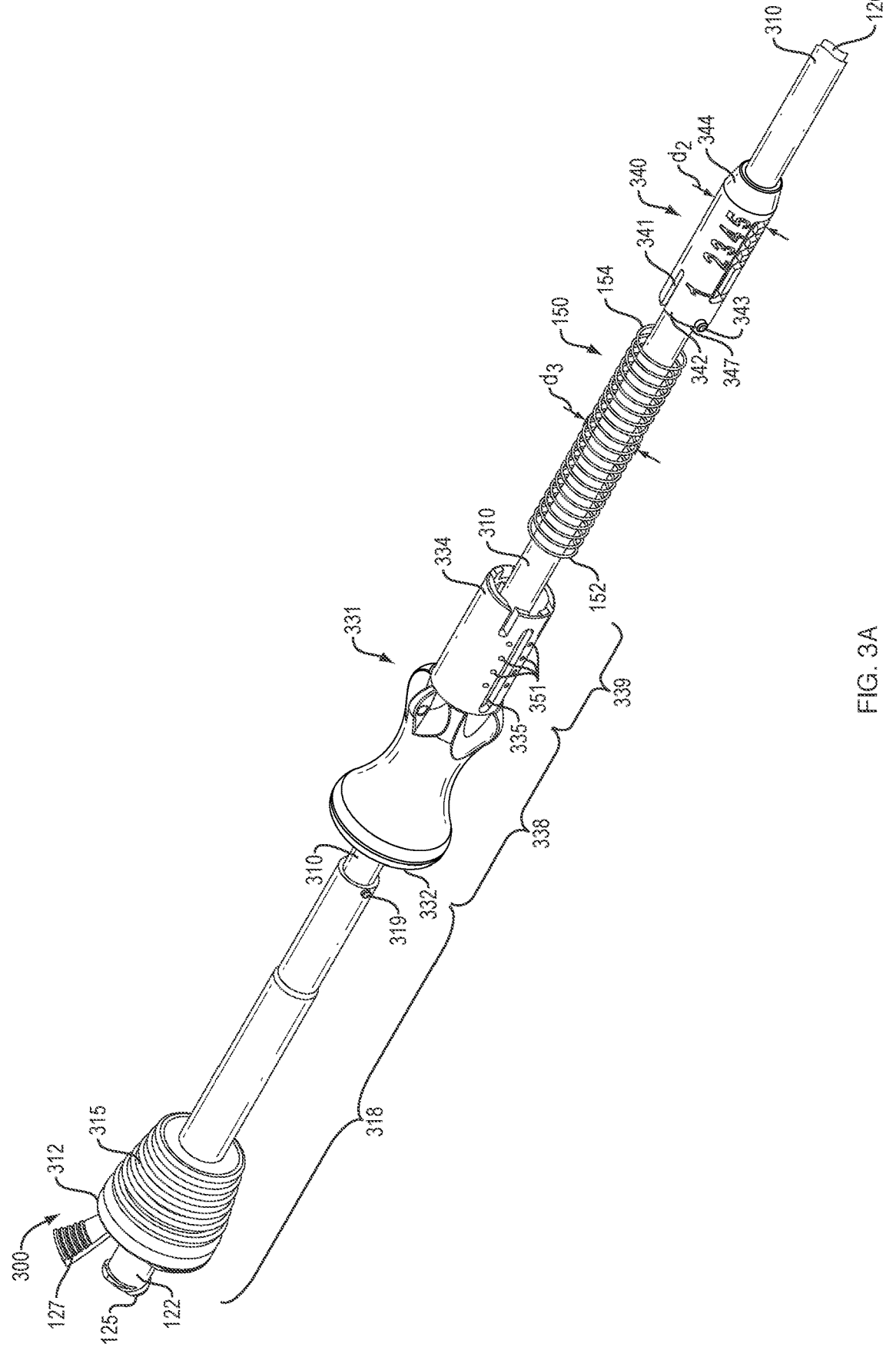
FIGS. 3A-3D provide perspective views of a medical device, according to one embodiment of the present disclosure.
Figure 3B:
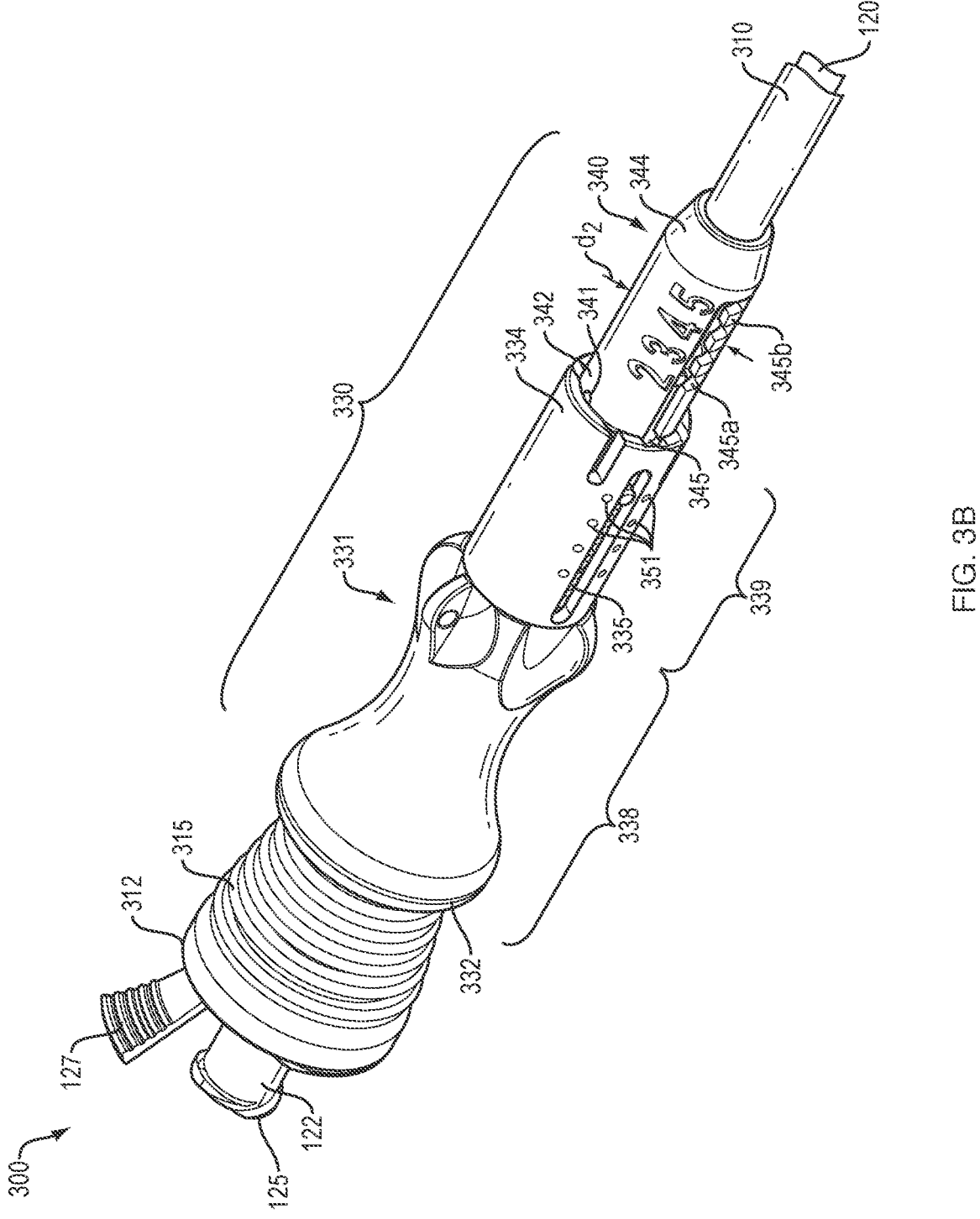
Figure 3C:
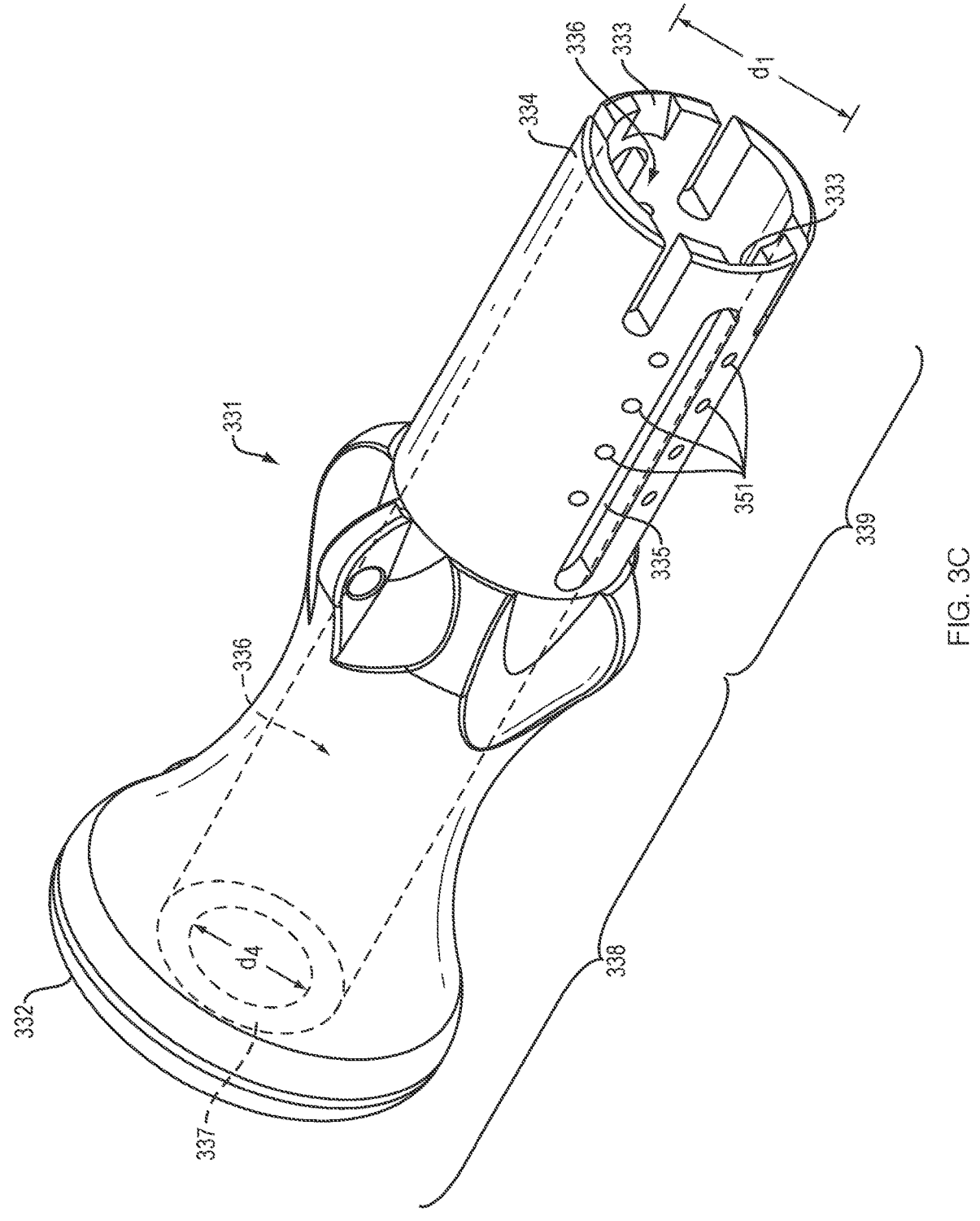
Figure 3D:
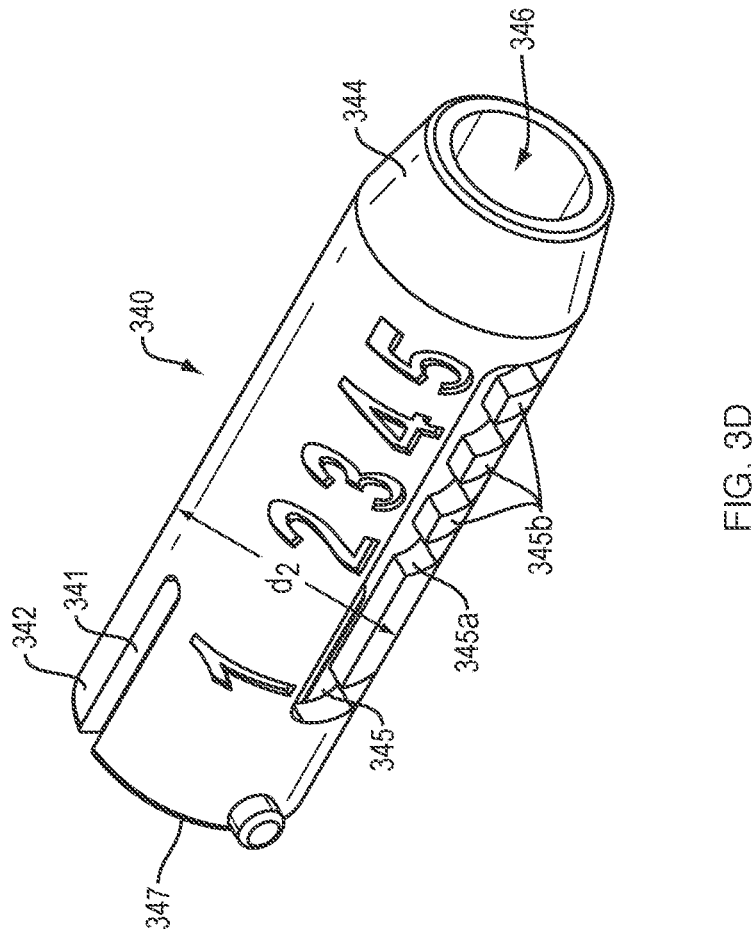
Figure 4A:
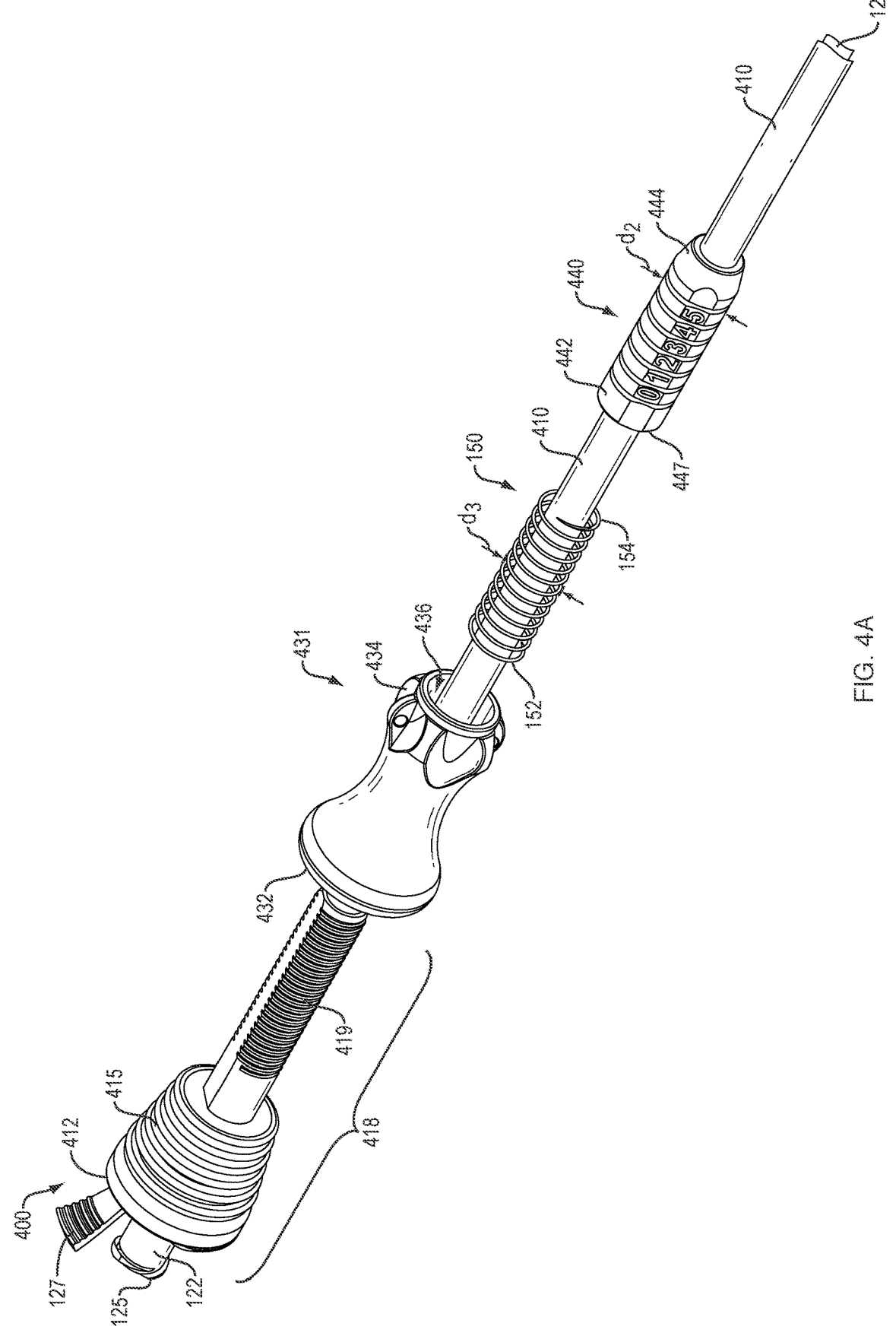
FIGS. 4A-4D provide perspective views of a medical device, according to one embodiment of the present disclosure.
Figure 4B:
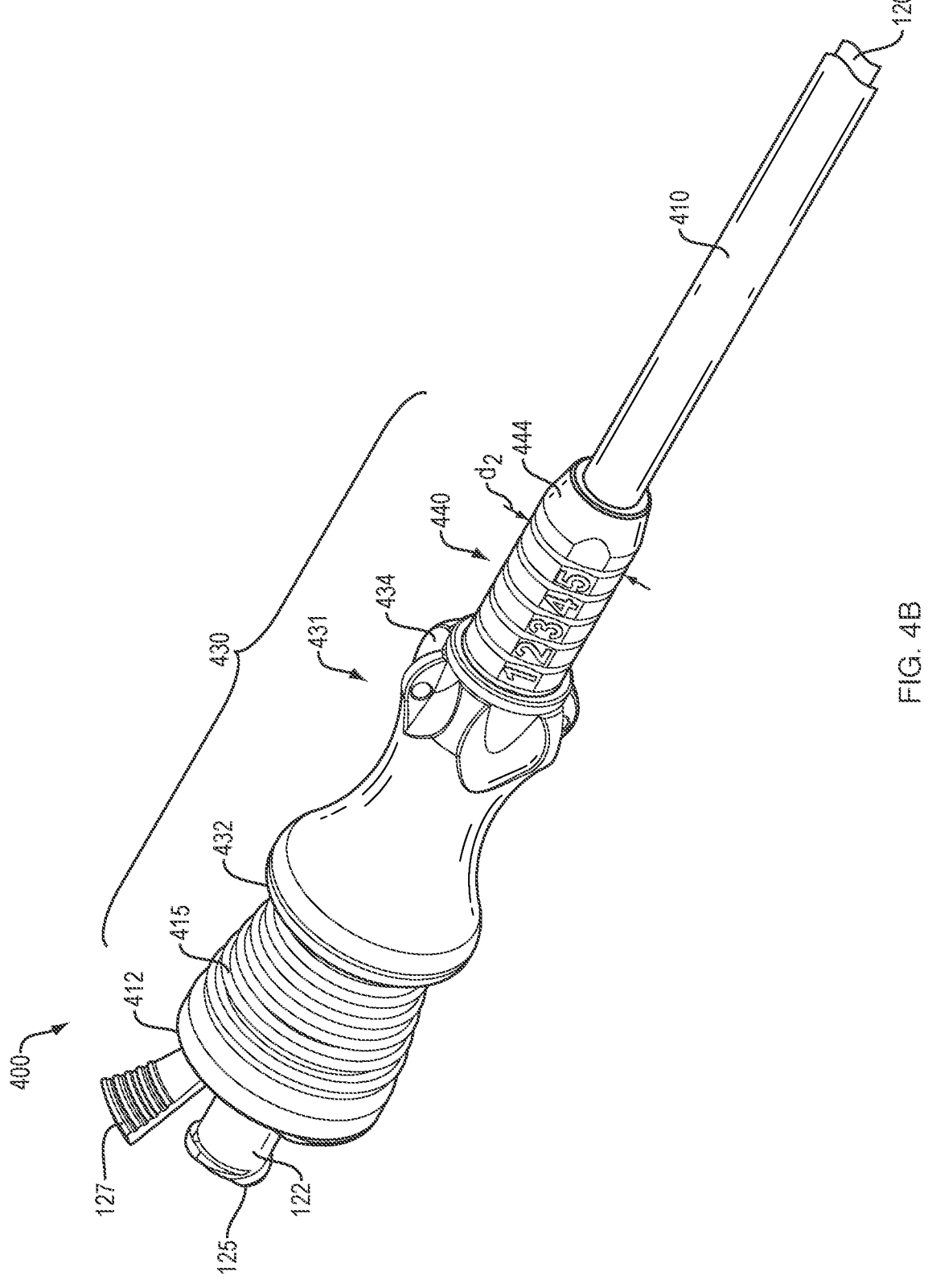
Figure 4C:
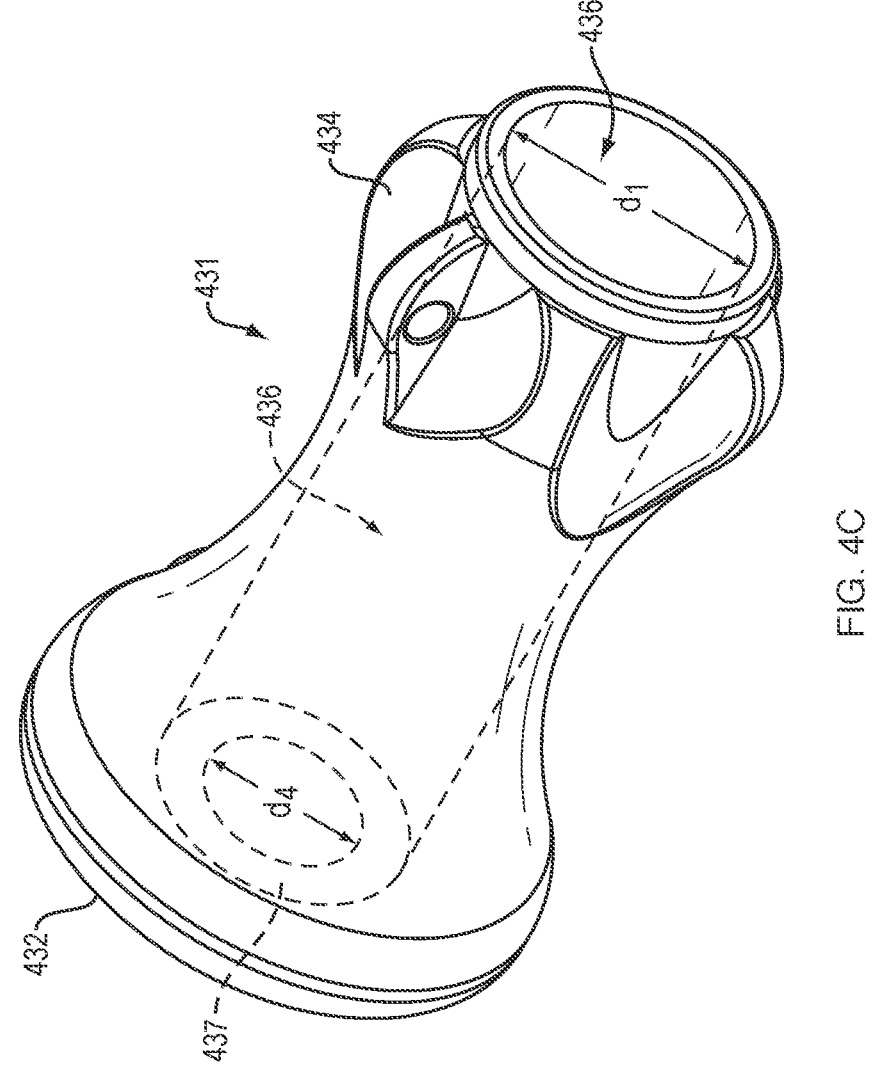
Figure 4D:
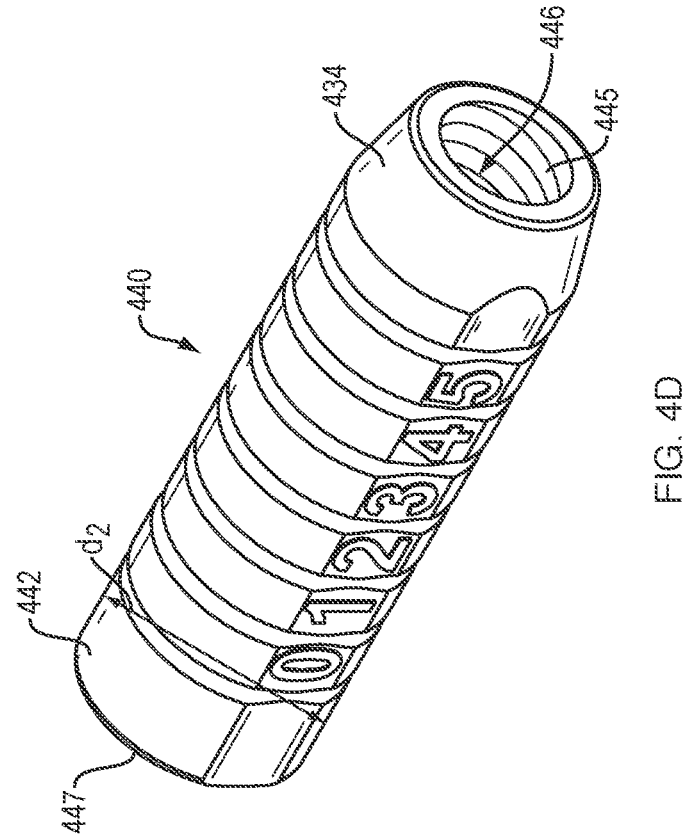
Figure 5A:
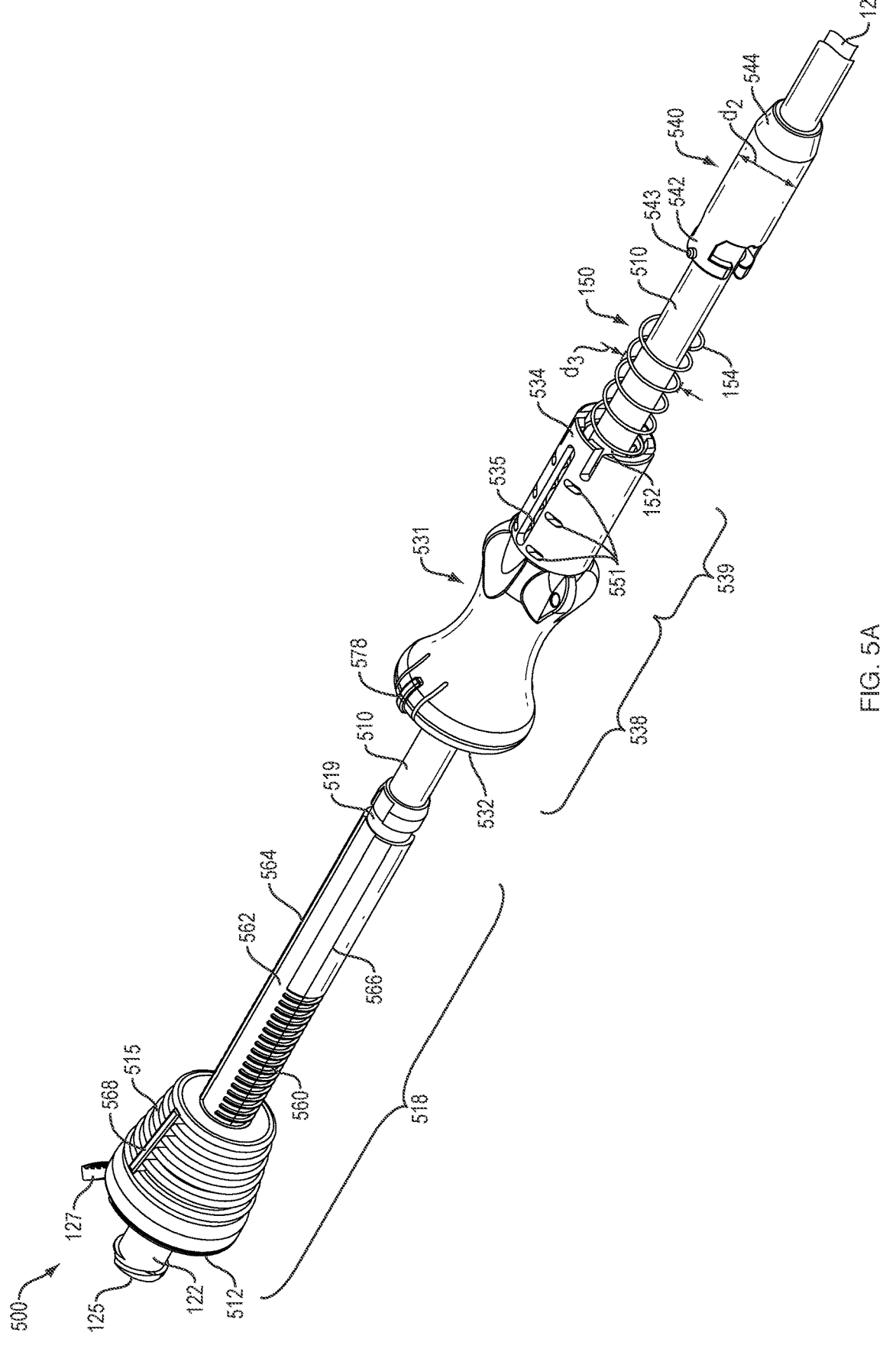
FIGS. 5A-5D provide perspective views of a medical device, according to one embodiment of the present disclosure.
Figure 5B:
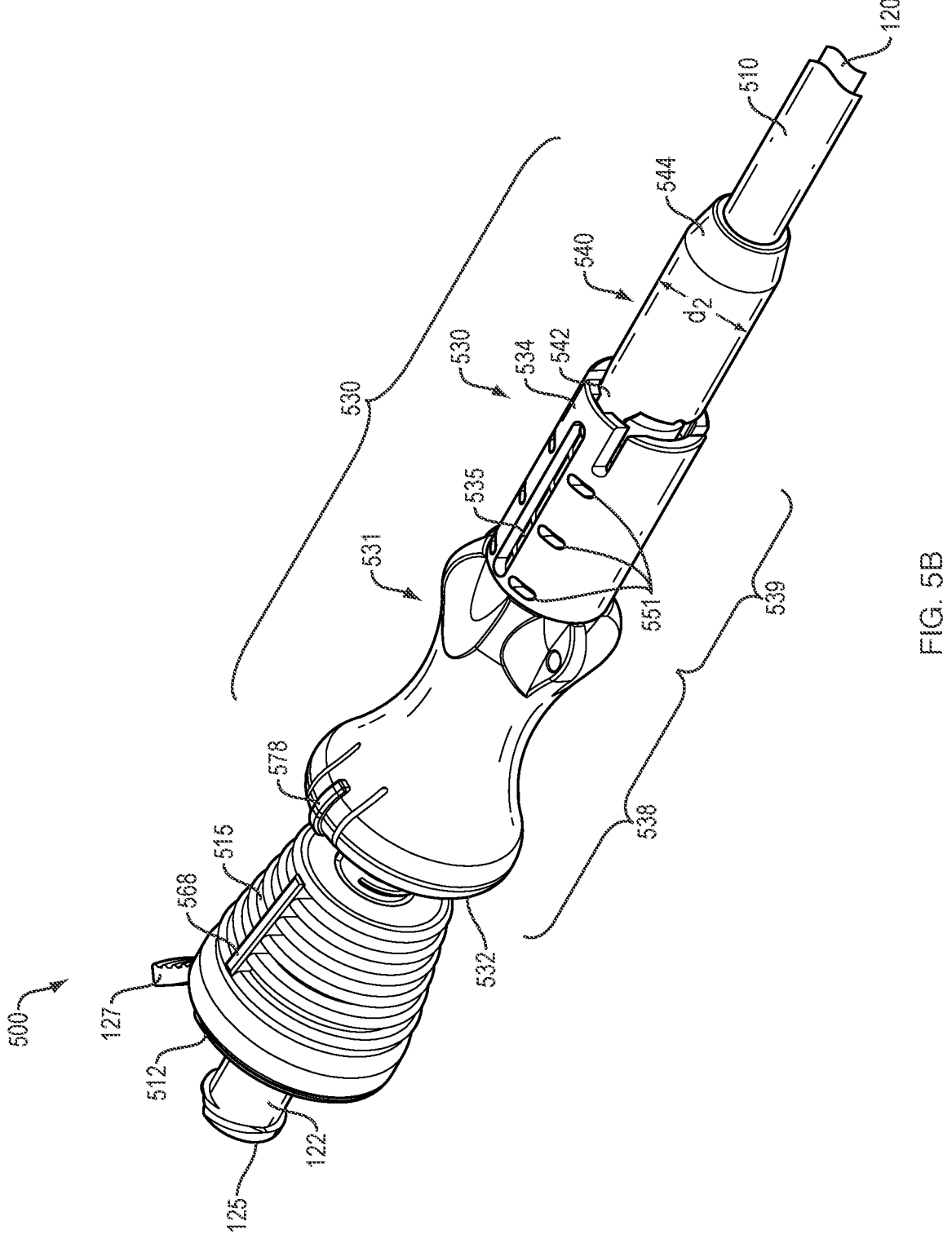
Figure 5C:
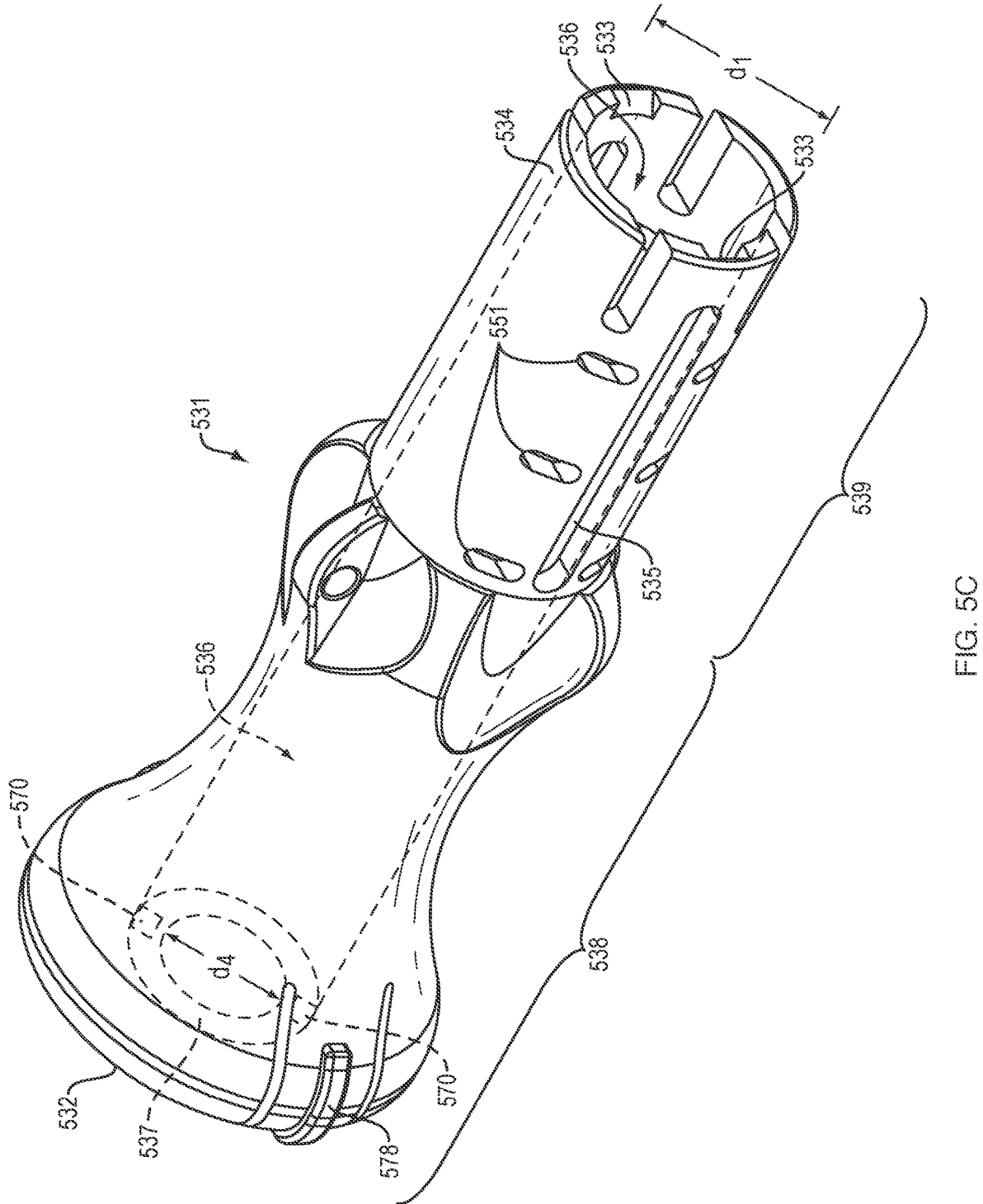
Figure 5D:
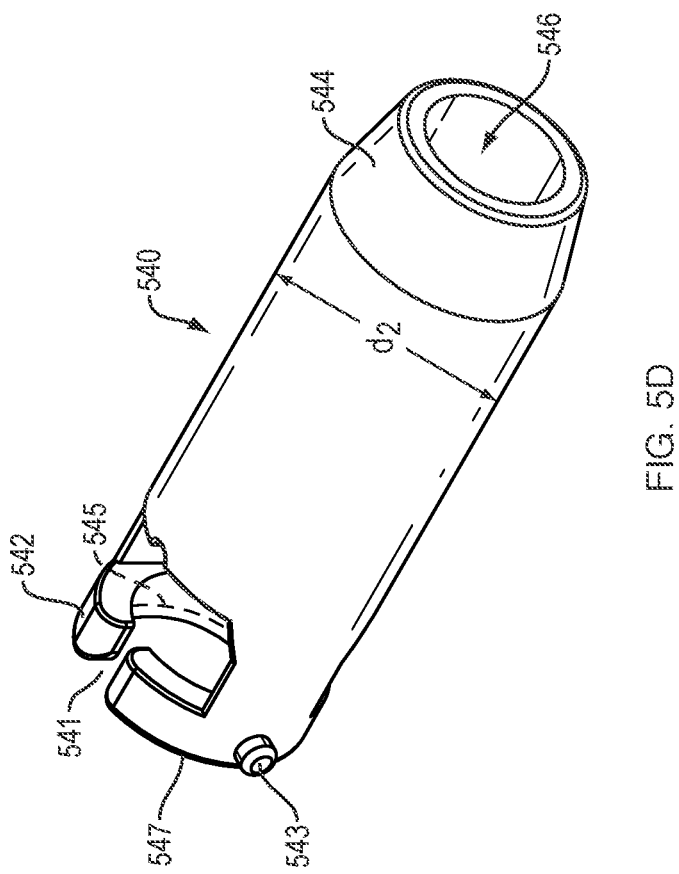

In various embodiments, the present disclosure relates to devices and methods to advance an access sheath and dilator through a body vessel, e.g., ureter, without exceeding a predetermined force that may perforate or otherwise damage the body vessel wall. Referring to FIG. 1, in one embodiment, a medical device 100 of the present disclosure may include an access sheath 110 comprising a proximal end 112, a distal end 114 and a lumen (not shown) extending therebetween. The proximal end 112 may include a sheath hub 115 insert molded or otherwise attached to a proximal portion 118 of the access sheath 110. The proximal portion 118 of the access sheath 110 may further include one or more surface features (not shown) configured to engage one or more corresponding mating features (not shown) of a cap 140, discussed below. A dilator 120 may be slidably disposed within the lumen of the access sheath 110. The dilator 120 may include a proximal end 122, a distal end 124 and a lumen, e.g., guidewire lumen (not shown), extending therebetween. The proximal end 122 may extend proximally beyond the proximal end 112 of the access sheath 110, and may include a dilator hub 125. The sheath hub 115 and/or dilator hub 125 may further include a lever or lock 127 configured to switch the access sheath 110 and dilator 120 between a locked and unlocked configuration. For example, in the locked configuration the dilator 120 may be fixedly disposed within the lumen of the access sheath 110, and in the unlocked configuration the dilator 120 may be free to slide/move within the lumen of the access sheath 110, e.g., for introduction through or removal from the access sheath 110. The distal end 124 of the dilator 120 may extend distally beyond the distal end 114 of the access sheath 110 and may include a tapered configuration, e.g., to facilitate atraumatic advancement through a narrow body passage.

In various embodiments, a force gauge 130 may be slidably disposed about the access sheath 110. The force gauge 130 may include a grip 131, a cap 140 and a compression resistance element, e.g., spring, elastic member, etc. (not shown). The grip 131 may include a proximal end 132, a distal end 134 and a lumen (not shown) extending therebetween. A spring abutment surface (not shown) may extend into the lumen at or near the proximal end 132 of the grip 131. In one embodiment, the grip 131 may include an ergonomic shape configured to accommodate the hand of a user. The ergonomic shape of the grip depicted in FIG. 1 is exemplary, and may include multiple shapes or designs to accommodate a variety of users. The cap 140 may be disposed about the access sheath 110 distal to the grip 131, and may include a proximal end 142, a distal end 144 and a lumen (not shown) extending therebetween. The proximal end 142 of the cap 140 may include a spring abutment surface (not shown). One or more mating features (not shown) may be disposed at or near the proximal end 142 of the cap 140 to reversibly engage the corresponding surface feature(s) on the proximal portion 118 of the access sheath 110. A spring as the compression resistant element may be disposed about the access sheath 110 between the grip 131 and cap 140, and may include a proximal end and a distal end (not shown). In one embodiment, the spring may include a free length ($L_1$), e.g., when in a relaxed configuration, substantially equal to a length of the lumen of the grip 131.

In one embodiment, the lumen of the grip 131 may include an inner dimension ($d_1$), the cap 140 may include an outer dimension ($d_2$) and the spring may include an outer dimension ($d_3$). The outer dimension ($d_1$) may be greater than the outer dimensions ($d_2$) and ($d_3$) such that the lumen 136 of the grip 131 may receive both the spring and cap 140. In one embodiment, the outer dimension ($d_3$) may be equal to or less than the outer dimension ($d_2$) such that the spring abutment surface at the proximal end 142 of the cap 140 may contact the distal end of the spring within the lumen of the grip 131.

In one embodiment, the medical device 100 may be assembled by proximally advancing the grip 131 over/along the access sheath 110 to place the proximal end 132 of the grip 131 in contact with, or adjacent to, a distal end of the sheath hub 115. The spring may then be proximally advanced into the lumen of the grip 131 to place the proximal end of the spring in contact with the spring abutment surface of the grip 131. The cap 140 may then be proximally advanced over/along the access sheath 110 to engage the mating feature(s) at or near the proximal end 142 of the cap 140 with the corresponding surface feature(s) on the proximal portion 118 of the access sheath 110. With the mating feature(s) of cap 140 engaged with the corresponding surface feature(s) of the access sheath 110, the distal end of the spring may be placed in contact with the spring abutment surface at the proximal end 142 of the cap 140. With the cap 140 locked to the proximal portion 118 of the access sheath 110, the grip 131 may move distally relative to the cap 140 and access sheath 110, to compress the spring within the lumen of the grip 131. A distance between the spring abutment surface of the grip 131 and the spring abutment surface of the cap 140 may be varied to increase or decrease a length of the spring within the lumen of the grip 131.

As used herein, the term "restoring force," refers to the force a compression spring exerts to return from a compressed state to the free length or equilibrium length ($L_1$). The restoring force (F) of a spring constrained at a length less than the equilibrium length ($L_1$) may be calculated using Hooke's Law (F=−kx), where (k) is the spring constant and (x) is the change in spring height from the free length. Stated differently, restoring force (F) refers to the "stiffness" of a spring. As a spring is compressed to a smaller height, the stiffness (e.g., restoring force) of the spring increases. In various embodiments, the initial height (e.g., compression) of the spring within the lumen of the grip 131 may be controlled by the initial distance between the spring abutment surfaces. For example, if the initial distance between the spring abutment surfaces is greater than or equal to the spring's equilibrium length (e.g., $L_1$), the non-compressed spring may have an initial restoring force (e.g., initial load, starting restoring force) of zero. Alternatively, if the initial distance between the spring abutment surfaces is less than the spring's equilibrium length, the compressed spring may have an initial restoring force greater than zero.

Referring to FIGS. 2A-2D, in one embodiment, a medical device 200 of the present disclosure may include an access sheath 210 comprising a proximal end 212, a distal end (not shown) and a lumen (not shown) extending therebetween. The proximal end 212 may include a sheath hub 215 insert molded or otherwise attached to a proximal portion 218 of the access sheath 210. The proximal portion 218 of the access sheath 210 may further include one or more surface features, e.g., protrusions 219, configured to engage one or more corresponding mating features of a cap 240, discussed below. A dilator 120 may be slidably disposed within the lumen of the access sheath 210, as discussed above. A proximal end 122 of the dilator 120 may extend proximally beyond the proximal end 212 of the access sheath 210, and may include a dilator hub 125. The sheath hub 215 and/or dilator hub 125 may further include a lever or lock 127 configured to switch the access sheath 210 and dilator 120 between a locked and unlocked configuration. For example, in the locked configuration the dilator 120 may be fixedly disposed within the lumen of the access sheath 210, and in the unlocked configuration the dilator 120 may be free to slide/move within the lumen of the access sheath 210, e.g., for introduction through or removal from the access sheath. The distal end (not shown) of the dilator 120 may extend distally beyond the distal end of the access sheath 210 and include a tapered configuration, e.g., to facilitate atraumatic advancement through a narrow body passage (e.g., ureter), as discussed above.

In various embodiments, a force gauge 230 may be slidably disposed about the access sheath 210. The force gauge 230 may include a grip 231, a cap 240 and a compression resistance element 150 (e.g., spring, elastic member, etc.). The grip 231 may include a proximal end 232, a distal end 234 and a lumen 236 extending therebetween. A spring abutment surface 237 may extend into the lumen 236 at or near the proximal end 232 of the grip 231. One or more ramped surfaces 233 may extend into the lumen 236 at or near the distal end 234 of the grip 231. In one embodiment, a proximal portion 238 of the grip 231 may include an outer surface with an ergonomic shape (as discussed above), and a distal portion 239 of the grip 231 may include one or more pin slots 235 extending through a wall of the grip 231 along a longitudinal axis of the distal portion 239. One or more incrementally spaced indicator marks 251 may be disposed on an outer surface of the grip 231 above and/or below the one or more pin slots 235.

The cap 240 may be disposed about the access sheath 210 distal to the grip 231, and may include a proximal end 242, a distal end 244 and a lumen 246 extending therebetween. The proximal end 242 of the cap 240 may include a spring abutment surface 247. One or more mating features, e.g., snap windows 245, may be formed within a wall of the cap 240 at or near the proximal end 242 to reversibly engage the corresponding protrusions 219 on the proximal portion 218 of the access sheath 210. One or more pins 243 may extend outward from an outer surface of the cap 240 at or near the proximal end 242, e.g., between the proximal end 242 and snap windows 245, and configured to be received within the corresponding one or more pin slots 235 of the grip 231. One or more relief slots 241 may extend along a longitudinal axis of the cap 240 from the proximal end 242, the relief slots configured to engage the corresponding ramped surfaces 233 within the lumen 236 of the grip 231. A spring 150 may be disposed about the access sheath 210 between the grip 231 and cap 240, and may include a proximal end 152 and a distal end 154.

In one embodiment, the lumen 236 of the grip 231 may include an inner dimension ($d_1$), the cap 240 may include an outer dimension ($d_2$) and the spring 150 may include an outer dimension ($d_3$). The inner dimension ($d_1$) may be greater than the outer dimensions ($d_2$) and ($d_3$) such that the lumen 236 of distal portion 239 of the grip 231 may receive both the spring 150 and cap 240. In one embodiment, the outer dimension ($d_3$) may be equal to or less than the outer dimension ($d_2$) such that the spring abutment surface 247 at the proximal end 242 of the cap 240 may contact the distal end 154 of the spring 150 within the lumen 236 of the distal portion 239 of the grip 231. The spring abutment surface 237 extending into the lumen 236 of the grip 231 may define an opening with an inner dimension ($d_4$) less than the outer dimension ($d_3$), e.g., such that the dilator 120 but not the spring 150 may pass through the opening.

In one embodiment, the medical device 200 may be assembled by proximally advancing the grip 231 over/along the access sheath 210 to place the proximal end 232 of the grip 231 in contact with, or adjacent to, a distal end of the sheath hub 215. The spring 150 may then be proximally advanced over/along the access sheath and into the lumen 236 of the grip 231 to place the proximal end 152 of the spring in contact with the spring abutment surface 237. The cap 240 may then be proximally advanced over/along the access sheath, the relief slots 241 aligned with the corresponding ramped surfaces 233, and the cap 240 proximally advanced through the lumen 236 of the distal portion 239 of the grip 231 until the snap windows 245 engage the corresponding protrusions 219 on the proximal portion 218 of the access sheath 210. The grip 231 may then be distally advanced until the one or more pins 243 engage (e.g., extend into) the corresponding one or more pin slots 235. With the snap windows 245 of cap 240 engaged with the corresponding protrusions 219 of the access sheath 210, the distal end 154 of the spring 150 may be placed in contact with the spring abutment surface 247 at the proximal end 242 of the cap 240.

In one embodiment, the initial distance between the spring abutment surface 237 of the grip 231, and the spring abutment surface 247 of the cap 240 may determine the initial restoring force (e.g., initial load) of the spring 150. For example, an initial distance between the spring abutment surfaces 237, 247 may be greater than or equal to the equilibrium length ($L_1$) of the spring 150, such that the initial restoring force of the spring 150 is zero. Alternatively, an initial distance between the spring abutment surfaces 237, 247 may include a distance less than the equilibrium length ($L_1$) of the spring 150, such that the spring is compressed (e.g., the initial height of the spring is less than the equilibrium length $L_1$) within the lumen 236 of the grip 231 at a predetermined initial restoring force greater than zero (e.g., 1.0 pounds).

With the cap 240 locked to the proximal portion 218 of the access sheath 210, the grip 231 may move distally relative to the cap and access sheath, to compress the spring 150 within the lumen 236. In various embodiments, a position of the pins 243 relative to one or more of the indicator marks 251 disposed above and/or below the respective pin slots 235 may correlate to a previously determined restoring force of the spring 150, and therefore the amount of resistive force exerted on the access sheath 210 and/or dilator 120, e.g., by an obstruction within the ureter. For example, when viewed from a proximal to distal end of the grip 231, a distance between each successive indicator mark 251 may correlate with a 0.50-pound decrease in restoring force. In various embodiments, the number of indicator marks, the spacing between the indicator marks and/or the length of the pin slots may be varied depending on the users need to distinguish incremental increases in restoring force.

Referring to FIGS. 3A-3D, in one embodiment, a medical device 300 of the present disclosure may include an access sheath 310 comprising a proximal end 312, a distal end (not shown) and a lumen (not shown) extending therebetween. The proximal end 312 may include a sheath hub 315 insert molded or otherwise attached to a proximal portion 318 of the access sheath 310. The proximal portion 318 of the access sheath 310 may further include one or more surface features e.g., protrusions 319, configured to engage one or more corresponding mating features of a cap 340, discussed below. A dilator 120 may be slidably disposed within the lumen of the access sheath 310, as discussed above. A proximal end 122 of the dilator 120 may extend proximally beyond the proximal end 312 of the access sheath 310, and may include a dilator hub 125. The sheath hub 315 and/or dilator hub 125 may further include a lever or lock 127 configured to switch the access sheath 310 and dilator 120 between a locked and unlocked configuration. For example, in the locked configuration the dilator 120 may be fixedly disposed within the lumen of the access sheath 310, and in the unlocked configuration the dilator 120 may be free to slide/move within the lumen of the access sheath 310, e.g., for introduction through or removal from the access sheath. The distal end (not shown) of the dilator 120 may extend distally beyond the distal end of the access sheath 310 and include a tapered configuration, e.g., to facilitate atraumatic advancement through a narrow body passage (e.g., ureter), as discussed above.

In various embodiments, a force gauge 330 may be slidably disposed about the access sheath 310. The force gauge 330 may include a grip 331, a cap 340 and a compression resistance element 150. The grip 331 may include a proximal end 332, a distal end 334 and a lumen 336 extending therebetween. A spring abutment surface 337 may extend into the lumen 336 at or near the proximal end 332 of the grip 331. One or more ramped surfaces 333 may extend into the lumen 336 at or near the distal end 334 of the grip 331. In one embodiment, a proximal portion 338 of the grip 331 may include an outer surface with an ergonomic shape (as discussed above), and a distal portion 339 of the grip 331 may include one or more pin slots 335 extending through a wall of the grip 331 along a longitudinal axis of the distal portion 339. One or more incrementally spaced indicator holes 351 may extend through a wall of the distal portion 339 of the grip 331 above and/or below the one or more pin slots 335.

The cap 340 may be disposed about the access sheath 310 distal to the grip 331, and may include a proximal end 342, a distal end 344 and a lumen 346 extending therebetween. The proximal end 342 of the cap 340 may include a spring abutment surface 347. One or more mating features (e.g., cap slots 345) may be formed within a wall of the cap 340. The cap slots 345 may further include a series of cross-slots 345a and protrusions 345b configured to reversibly engage the corresponding protrusions 319 on the proximal portion 318 of the access sheath 310. A series of indicator numbers (e.g., 1, 2, 3, 4, 5) may be included on an outer surface of the cap 340 to individually identify each of the cross-slots 345a. One or more pins 343 may extend outward from an outer surface of the cap 340 at or near the proximal end 342, e.g., between the proximal end 342 and cap slot(s) 345, the pins 343 may be configured to be received within the corresponding pin slot(s) 335 of the grip 331. One or more relief slots 341 may extend along a longitudinal axis of the cap 340 from the proximal end 342, the relief slots 341 may be configured to engage the corresponding ramped surfaces 333 within the lumen 336 of the grip 331. The spring 150 may be disposed about the access sheath 310 between the grip 331 and cap 340, and may include a proximal end 152 and a distal end 154.

In one embodiment, the lumen 336 of the grip 331 may include an inner dimension ($d_1$), the cap 340 may include an outer dimension ($d_2$) and the spring 150 may include an outer dimension ($d_3$). The inner dimension ($d_1$) may be greater than the outer dimensions ($d_2$) and ($d_3$) such that the lumen 336 of distal portion 339 of the grip 331 may receive both the spring 150 and cap 340. In one embodiment, the outer dimension ($d_3$) may be equal to or less than the outer dimension ($d_2$) such that the spring abutment surface 347 at the proximal end 342 of the cap 340 may contact the distal end 154 of the spring 150 within the lumen 336 of the distal portion 339 of the grip 331. The spring abutment surface 337 extending into the lumen 336 of the grip 331 may define an opening with an inner dimension ($d_4$) less than the outer dimension ($d_3$), e.g., such that the dilator 120 but not the spring 150 may pass through the opening.

In one embodiment, the medical device 300 may be assembled by proximally advancing the grip 331 over/along the access sheath 310 to place the proximal end 332 of the grip 331 in contact with, or adjacent to, a distal end of the sheath hub 315. The spring 150 may then be proximally advanced over/along the access sheath and into the lumen 336 of the grip 331 to place the proximal end 152 in contact with the spring abutment surface 337. The cap 340 may then be proximally advanced over/along the access sheath, the relief slots 341 aligned with the corresponding ramped surfaces 333 and the cap 340 proximally advanced through the lumen 336 of the distal portion 339 of the grip 331 until the cross-slots 345*a* engage the corresponding protrusions 319 on the proximal portion 318 of the access sheath 310. The grip 331 may then be distally advanced until the one or more pins 343 engage (e.g., extend into) the corresponding one or more pin slots 335. With the cross-slots 345*a* engaged with the corresponding protrusions 319 of the access sheath 310, the distal end 154 of the spring 150 may be placed in contact with the spring abutment surface 347 at the proximal end 342 of the cap 340.

In one embodiment, the initial distance between the spring abutment surface 337 of the grip 331 and the spring abutment surface 347 of the cap 340 may determine the initial restoring force of the spring 150. For example, when the protrusions 319 are disposed within respective cross-slot 345*a* identified by indicator number 1, an initial distance between the spring abutment surfaces 337, 347 may be greater than or equal to the equilibrium length ($L_1$) of the spring 150, such that the initial restoring force of the spring 150 is zero. The cap may be moved to place the protrusions 319 within cross-slots 345*a* identified by indicator numbers 2, 3 4 or 5 to incrementally decrease the distance between the spring abutment surfaces 337, 347 such that the spring 150 is compressed within the lumen 336 of the grip at various predetermined initial restoring forces greater than zero. For example, the increased distance between cross-slots 345*a* identified by indicator numbers 1 (e.g., initial distance) and 2 (e.g., second distance) may represent the decrease in distance between the spring abutment surfaces 337, 347 required to move the spring 150 from an initial height, with an equilibrium length ($L_1$) and an initial restoring force of zero, to a second height at which the spring 150 is compressed within the lumen 336 of the grip 331 at a predetermined initial restoring force greater than zero (e.g., 1.0 pounds). The distance between the evenly spaced cross-slots 345*a* identified by indicator numbers 2 (e.g., second distance), 3 (e.g., third distance), 4 (e.g., fourth distance) and 5 (e.g., fifth distance) may represent respective distances between the spring abutment surfaces 337, 347 at which the spring 150 is compressed within the lumen 336 of the grip 331 at predetermined initial restoring forces of 1.5 pounds (e.g., cross-slot 345*a* identified by indicator line 2), 2.0 pounds (e.g., cross-slot 345*a* identified by indicator line 3), 2.5 pounds (e.g., cross-slot 345*a* identified by indicator line 4) and 3.0 pounds (e.g., cross-slot 345*a* identified by indicator line 5).

With the cap 340 locked to the proximal portion 318 of the access sheath 310, the grip 331 may move distally relative to the cap and access sheath to compress the spring 150 within the lumen 336. In various embodiments, a position of the pins 343 relative to each of the indicator holes 351 disposed above and/or below the respective pin slots 335 may correlate to a previously determined initial restoring force of the spring 150, and therefore the amount of resistive force exerted on the access sheath 310 and/or dilator 120, e.g., by an obstruction within the ureter. For example, when viewed from a proximal to distal end of the grip 331, a distance between each successive indicator hole 351 may correlate with a 0.50-pound decrease in initial restoring force. In various embodiments, the number of indicator marks, the spacing between the indicator marks and/or the length of the pin slots may be varied depending on the users need to distinguish incremental increases in restoring force.

Referring to FIGS. 4A-4D, in one embodiment, a medical device 400 of the present disclosure may include an access sheath 410 comprising a proximal end 412, a distal end (not shown) and a lumen (not shown) extending therebetween. The proximal end 412 may include a sheath hub 415 insert molded or otherwise attached to a proximal portion 418 of the access sheath 410. The proximal portion 418 of the access sheath 410 may further include a surface feature, e.g., threaded groove 419, configured to engage a corresponding mating feature of a cap 440, discussed below. A dilator 120 may be slidably disposed within the lumen of the access sheath 410, as discussed above. A proximal end 122 of the dilator 120 may extend proximally beyond the proximal end 412 of the access sheath 410, and may include a dilator hub 125. The sheath hub 415 and/or dilator hub 125 may further include a lever or lock 127 configured to switch the access sheath 410 and dilator 120 between a locked and unlocked configuration. For example, in the locked configuration the dilator 120 may be fixedly disposed within the lumen of the access sheath 410, and in the unlocked configuration the dilator 120 may be free to slide/move within the lumen of the access sheath 410, e.g., for introduction through or removal from the access sheath. The distal end of the dilator 120 may extend distally beyond the distal end of the access sheath 410 and include a tapered configuration, e.g., to facilitate atraumatic advancement through a narrow body passage (e.g., ureter), as discussed above.

In various embodiments, a force gauge 430 may be slidably disposed about the access sheath 410. The force gauge 430 may include a grip 431, a cap 440 and a compression resistance element, such as spring 150. The grip 431 may include a proximal end 432, a distal end 434 and a lumen 436 extending therebetween. A spring abutment surface 437 may extend into the lumen 436 at or near the proximal end 432 of the grip 431. In one embodiment, the grip 431 may include an outer surface with an ergonomic shape (as discussed above).

The cap 440 may be disposed about the access sheath 410 distal to the grip 431, and may include a proximal end 442, a distal end 444 and a lumen 446 extending therebetween. The proximal end 442 of the cap 440 may include a spring abutment surface 447. An inner surface of the cap 440 may include a mating feature, e.g., threads 445, configured to be received within the corresponding threaded groove 419 on the proximal portion 418 of the access sheath 410. A series of indicator numbers (e.g., 0, 1, 2, 3, 4, 5) may be included on an outer surface of the cap 440 to individually identify a position of the cap 430 along the access sheath 410. The spring 150 may be disposed about the access sheath 410 between the grip 431 and cap 340, and may include a proximal end 152 and a distal end 154.

In one embodiment, the lumen 436 of the grip 431 may include an inner dimension ($d_1$), the cap 440 may include an outer dimension ($d_2$) and the spring 150 may include an outer dimension ($d_3$). The inner dimension ($d_1$) may be greater than the outer dimensions ($d_2$) and ($d_3$) such that the lumen 436 of the grip 431 may receive both the spring 150 and cap 440. In one embodiment, the outer dimension ($d_3$)

may be equal to or less than the outer dimension ($d_2$) such that the spring abutment surface 447 at the proximal end 442 of the of the cap 440 may contact the distal end 154 of the spring 150 within the lumen 436 of the grip 431. The spring abutment surface 437 extending into the lumen 436 of the grip 431 may define an opening with an inner dimension ($d_4$) less than the outer dimension ($d_3$), e.g., such that the dilator 120 but not the spring 150 may pass through the opening.

In one embodiment, the medical device 400 may be assembled by proximally advancing the grip 431 over/along the access sheath 410 to place the proximal end 432 of the grip 431 in contact with, or adjacent to, a distal end of the sheath hub 415. The spring 150 may then be proximally advanced over/along the access sheath and into the lumen 436 of the grip 431 to place the proximal end 152 in contact with the spring abutment surface 437. The cap 440 may then be further proximally advanced over/along the access sheath into the lumen 436 of the grip 431 until the threads 445 on the proximal end 442 of the cap 440 engage the corresponding threaded groove 419 on the proximal portion 418 of the access sheath 410. With the threads 445 of the cap 440 engaged with the corresponding threaded groove 419 of the access sheath 410, the distal end 154 of the spring 150 may be placed in contact with the spring abutment surface 447 at the proximal end 442 of the cap 440. The cap 440 may be proximally advanced along the access sheath 410 by rotating the cap 440 in a first direction (e.g., clockwise), and distally advanced along the access sheath 410 by rotating the cap 440 in a second direction (e.g., counterclockwise).

In one embodiment, the initial distance between the spring abutment surface 437 of the grip 431 and the spring abutment surface 447 of the cap 440 may determine the initial restoring force of the spring 150. For example, when the cap 440 is rotated along the access sheath 410 such that the distal end 434 of the grip 431 aligns with the indicator number 0, an initial distance between the spring abutment surfaces 437, 447 may be greater than or equal to the equilibrium length ($L_1$) of the spring 150, such that the initial restoring force of the spring 150 is zero. The cap 440 may be further rotated in the first direction to incrementally decrease the distance between the spring abutment surfaces 437, 447 to further decrease a height of the spring 150 within the lumen 436 of the grip 431. When aligned with the distal end 434 of the grip 431, each indicator number may correlate to a different predetermined initial restoring force of the spring greater than zero. For example, the distance between indicator number 0 (e.g., initial distance) and indicator number 1 (e.g., second distance) may represent the decrease in distance between the spring abutment surfaces 437, 447 required to move the spring from an initial height with an equilibrium length ($L_1$) and an initial restoring force of zero, to a second height at which the spring 150 is compressed within the lumen 436 of the grip 431 at a predetermined initial restoring force greater than zero (e.g., 1.0 pounds). The distance between the evenly spaced indicator numbers 2 (e.g., third distance), 3 (e.g., fourth distance), 4 (e.g., fifth distance) and 5 (e.g., sixth distance) may represent respective distances between the spring abutment surfaces 437, 447 at which the spring 150 is compressed within the lumen 436 of the grip 431 at predetermined initial restoring forces of 1.5 pounds (e.g., indicator number 2), 2.0 pounds (e.g., indicator number 3), 2.5 pounds (e.g., indicator number 4) and 3.0 pounds (e.g., indicator number 5). In one embodiment, a proximal portion of the cap 440 (e.g., between the proximal end 442 and indicator number 0) may include a color or color gradient (e.g., red, etc.) to alert a user that further rotation of the cap 440 in the distal direction may result in the cap 440 separating from the access sheath 410, e.g., as the threads 445 disengage the threaded grooves 419.

With the cap 440 secured to the proximal portion 418 of the access sheath 410 and maintaining the spring at a height corresponding to a previously determined initial restoring force, the grip 431 may move distally relative to the cap and access sheath to compress the spring 150 within the lumen 436. In various embodiments, a position of the distal end 434 of the grip 431 relative to indicator numbers 0-5 on the cap 430 may correlate to a previously determined restoring force of the spring, and therefore the amount of resistive force exerted on the access sheath 410 and/or dilator 120, e.g., by an obstruction within the ureter, as discussed above.

Referring to FIGS. 5A-5D, in one embodiment, a medical device 500 of the present disclosure may include an access sheath 510 comprising a proximal end 512, a distal end (not shown) and a lumen (not shown) extending therebetween. The proximal end 512 may include a sheath hub 515 insert molded or otherwise attached to a proximal portion 518 of the access sheath 510. An outer surface of the sheath hub 515 may include a release slot indicator 568. A series of surface features, e.g., ratchet teeth 560, may be disposed along opposite sides (e.g., separated by 180°) of the proximal portion 518 of the access sheath 510, and configured to engage one or more corresponding ratchet catches 570 of a grip 531, discussed below. In one embodiment, a surface of each of the ratchet teeth 560 may include an inclined slope in the distal direction, e.g., a height of a distal end of each ratchet tooth is greater than a height of a proximal end of each ratchet tooth. A ratchet release slot 562 may be disposed along opposite sides (e.g., separated by 180°) of the proximal portion 518 of the access sheath 510 between each series of ratchet teeth 560. A first stop edge 564 may extend along a longitudinal axis of the proximal portion 518 of the access sheath 510, e.g., along an edge of one of the ratchet release slots 562. A second stop edge 566 may extend along a longitudinal axis of the proximal portion 518 of the access sheath 510. In one embodiment, the first and second stop edges 564, 566 may be separated along the longitudinal axis of the proximal portion 518 of the access sheath 510 by less than 180° (e.g., separated by approximately 90°). The proximal portion 518 may further include a recess 519 extending around a circumference of the access sheath 510. A dilator 120 may be slidably disposed within the lumen of the access sheath 510, as discussed above. The proximal end 122 of the dilator 120 may extend proximally beyond the proximal end 512 of the access sheath 510, and may include a dilator hub 125. The sheath hub 515 and/or dilator hub 125 may further include a lever or lock 127 configured to switch the access sheath 510 and dilator 120 between a locked and unlocked configuration. For example, in the locked configuration the dilator 120 may be fixedly disposed within the lumen of the access sheath 510, and in the unlocked configuration the dilator 120 may be free to slide/move within the lumen of the access sheath 510, e.g., for introduction through or removal from the access sheath. The distal end of the dilator 120 may extend distally beyond the distal end of the access sheath 510 and include a tapered configuration, e.g., to facilitate atraumatic advancement through a narrow body passage (e.g., ureter), as discussed above.

In various embodiments, a force gauge 530 may be slidably disposed about the access sheath 510. The force gauge 530 may include a grip 531, a cap 540 and a compression resistance element 150. The grip 531 may include a proximal end 532, a distal end 534 and a lumen 536 extending therebetween. A spring abutment surface 537 may extend into the lumen 536 at or near the proximal end 532 of the grip 531. One or more ratchet catches 570 may extend into the lumen 536 at or near the proximal end 532 of the grip 531 and proximal to the spring abutment surface 537. An outer surface of the grip 531 may include one or more catch indicators 578 aligned with the corresponding ratchet catches 570. One or more ramped surfaces 533 may extend into the lumen 536 at or near the distal end 534 of the grip 531. In one embodiment, a proximal portion 538 of the grip 531 may include an outer surface with an ergonomic shape (as discussed above), and a distal portion 539 of the grip 531 may include one or more pin slots 535 extending through a wall of the grip 531 along a longitudinal axis of the distal portion 539. A series of incrementally spaced indicator holes 551 may extend through a wall of the distal portion 539 of the grip 531 above and/or below the one or more pin slots 535.

The cap 540 may be disposed about the access sheath 510 distal to the grip 531, and may include a proximal end 542, a distal end 544 and a lumen 546 extending therebetween. The proximal end 542 of the cap 540 may include a spring abutment surface 547. A collar 545 may extend along an inner surface of the cap 540 at or near the proximal end 542. One or more pins 543 may extend outward from an outer surface of the cap 540 at or near the proximal end 542, and may be configured to be received within the corresponding one or more pin slots 535 of the grip 531. One or more relief slots 541 may extend along a longitudinal axis of the cap 540 from the proximal end 542, and may be configured to engage the corresponding ramped surfaces 533 of the lumen 536 of the grip 531. The spring 150 may be disposed about the access sheath 510 between the grip 531 and cap 540, and may include a proximal end 152 and a distal end 154.

In one embodiment, the lumen 536 of the grip 531 may include an inner dimension ($d_1$), the cap 540 may include an outer dimension ($d_2$) and the spring 150 may include an outer dimension ($d_3$). The inner dimension ($d_1$) may be greater than the outer dimensions ($d_2$) and ($d_3$) such that the lumen 536 of distal portion 539 of the grip 531 may receive both the spring 150 and cap 540. In one embodiment, the outer dimension ($d_3$) may be equal to or less than the outer dimension ($d_2$) such that the spring abutment surface 547 at the proximal end 542 of the cap 540 may contact the distal end 154 of the spring 150 within the lumen 536 of the distal portion 539 of the grip 531. The spring abutment surface 537 extending into the lumen 536 of the grip 531 may define an opening with an inner dimension ($d_4$) less than the outer dimension ($d_3$), e.g., such that the dilator 120 but not the spring 150 may pass through the opening.

In one embodiment, the medical device 500 may be assembled by aligning the catch indicator 578 on the outer surface of the grip 531 with the release slot indicator 568 of the sheath hub 515, thereby aligning the ratchet catches 570 with the respective ratchet release slots 562, and placing one of the ratchet catches in contact with the first stop edge 564. The grip 531 may be proximally advanced over/along the access sheath 510 to place the proximal end 532 of the grip 531 in contact with, or adjacent to, a distal end of sheath hub 515. The spring 150 may then be proximally advanced into the lumen 536 of the grip 531 to place the proximal end 152 in contact with the spring abutment surface 537. The cap 540 may then be proximally advanced over/along the access sheath, the relief slots 541 aligned with the corresponding ramped surfaces and the cap 540 proximally advanced through the lumen 536 of the distal portion 539 of the grip 531 to place the collar 545 within the circular recess 519 on the distal portion 518 of the access sheath 510. The grip 531 may then be distally advanced until the one or more pins 543 engage (e.g., extend into) the corresponding one or more pin slots 535.

With the collar 545 of the cap 540 rotatably disposed within the circular recess 519 of the access sheath 510, the ratchet catches 570 disposed within the corresponding ratchet release slots 562, and one of the ratchet catches in contact with the first stop edge 564, the force gauge 530 may be in a "non-ratchet" mode. An initial distance between the spring abutment surfaces 537, 547 in the "non-ratchet" mode may be greater than or equal to the equilibrium length ($L_1$) of the spring 150, such that the initial restoring force of the spring is zero. In the "non-ratchet" mode, the grip 531 may be move proximally and/or distally relative to the cap and access sheath as necessary to increase or decrease a height of the spring within the lumen 536.

In one embodiment, the force gauge 530 may switch from the "non-ratchet" mode to a "ratchet" mode by rotating the grip 531 to place the ratchet catch 570 in contact with the second stop edge 566, such that both ratchet catches 570 are placed in contact with a corresponding series of ratchet teeth 560. In the "ratchet mode" the grip 531 may move distally relative to the cap and access sheath as the ratchet catches 570 slide over the inclined outer surface(s) of successive ratchet teeth 560. As the grip 531 moves distally relative to the cap and access sheath, an increase in the initial restoring force of the spring 150 may be determined based on a position of the pins 543 of the cap 540 relative to the corresponding indicator markers 551 above and/or below the pin slot 535. In addition, or alternatively, an audible click or tactile feel may indicate distal movement of the grip 531 relative to the cap and access sheath as the ratchet catches 570 move across/over successive ratchet teeth 560. The inclined outer surface of each ratchet tooth may prevent the grip 531 from moving proximally relative to the cap and access sheath, e.g., if the grip 531 is released. In one embodiment, the ability of the ratchet teeth 560 to prevent the grip 531 from moving proximally relative to the cap and access sheath may prevent inadvertent recoil of the spring 150, which may be translated to the access sheath 510 and/or dilator 120 within the patient. The force gauge 530 may be returned to the "non-ratchet" mode by rotating the grip 531 to place the ratchet catch in contact with the first stop edge 564, and position the ratchet catches 570 within the respective ratchet release slots 562.

In various embodiments, the present disclosure relates to devices and methods to measure ureteral distensibility (e.g., ureteric calibration) to distinguish a non-distensible or "difficult" ureter from a distensible ureter. As used herein, a "distensible ureter" may refer to a ureter through which a dilator of 10 French or greater may be advanced, and a "non-distensible ureter" may refer to a ureter through which a dilator of 10 French or less may not be advanced, e.g., more than 2-6 cm from the ureteric orifice. In various embodiments, determining ureteric distensibility prior to performing a ureteroscopy procedure may identify patients with non-distensible or "difficult ureters," in which a pre-stenting or secondary ureteroscopy procedure may result in a more favorable medical outcome (See, for example, "Outcome of ureteral distensibility on the success of ureteroscopy: A prospective hospital-based descriptive study," African Journal of Urology (2017), vol. 23, pages 33-27; herein incorporated by reference in its entirety).

Figure 6A:
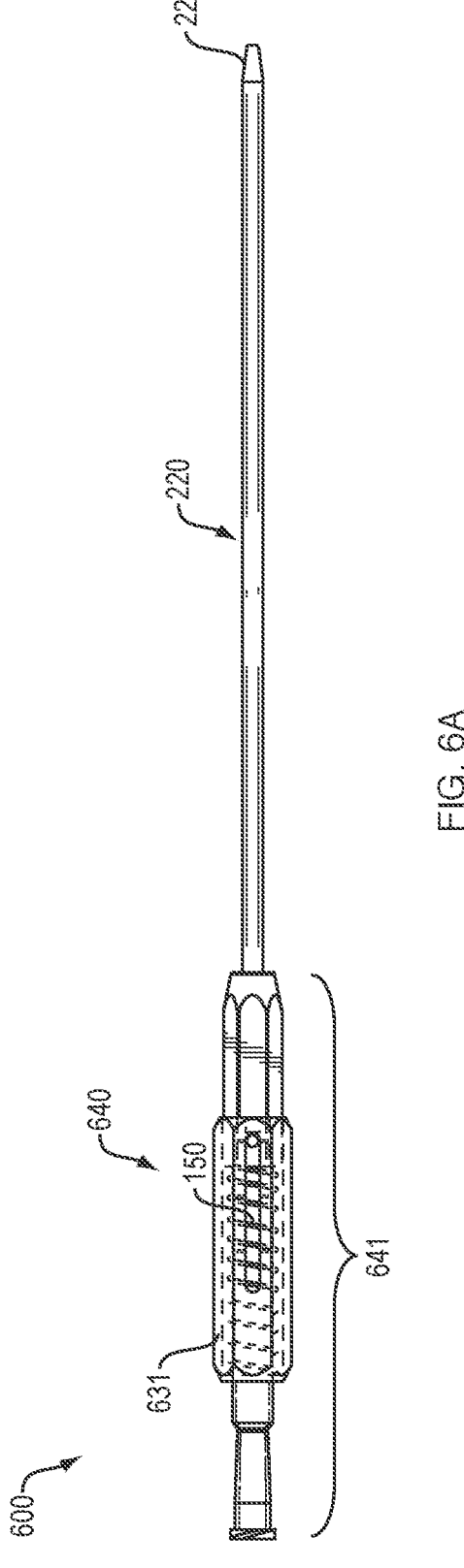
FIGS. 6A-6E provide perspective views of a medical device, according to one embodiment of the present disclosure.

Referring to FIG. 6A, in one embodiment, a medical device 600 of the present disclosure may include a force gauge 640 attached to a 10 French dilator 220. The dilator 220 may include a proximal end 222 (FIG. 6D), a distal end 224 and a lumen, e.g., guidewire lumen (not shown), extending therebetween. The distal end 224 of the dilator 220 may include a tapered configuration, e.g., to facilitate atraumatic advancement through a narrow body passage. In various embodiments, the force gauge 640 may include a shaft 641, a grip 631 and a compression resistance element 150, e.g., a spring, elastic member, etc.

Figure 6B:
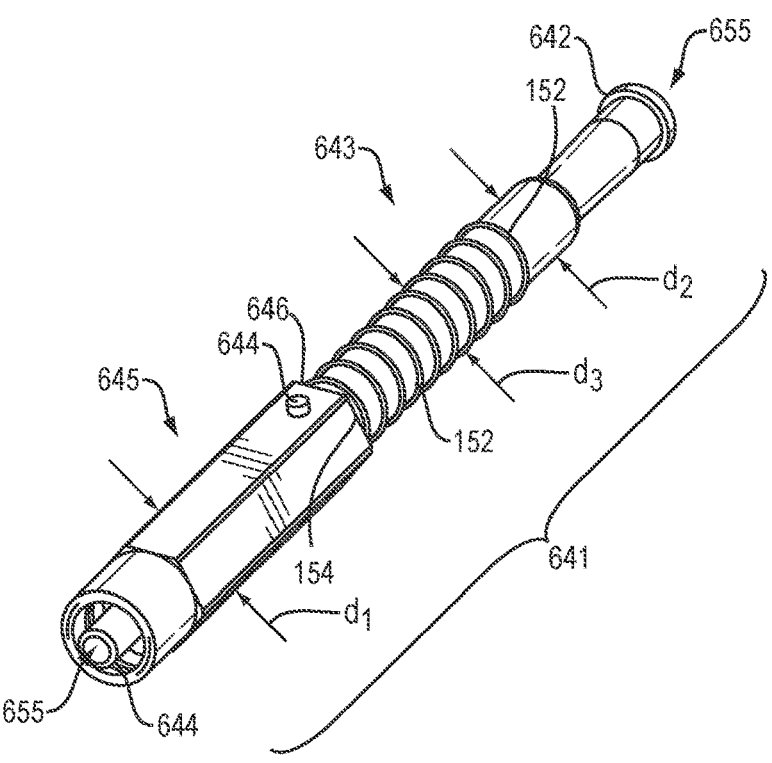

Referring to FIG. 6B, in one embodiment, the shaft 641 may include a proximal end 642 with a female luer connector, a distal end 644 with a male luer connector and a lumen 655 extending therebetween. The male luer connector may be configured to receive a corresponding female luer connector (not shown) on the proximal end of the dilator, such that dilators of different size (e.g., 8 French, 9 French, etc.), shape and/or length may be attached to and removed from the force gauge, e.g., during or prior to a medical procedure. Alternatively, referring to FIG. 6D, in one embodiment a proximal portion 223 of the dilator 220 may be permanently or removably disposed within at least a portion the lumen 655 of the shaft 641. For example, in various embodiments, the shaft 641 may be glued, swaged, wedged, compression fit, screwed and/or insert molded over the proximal portion 223 of the dilator 220. The shaft 641 may include a distal portion 645 with an outer dimension ($d_1$) and a proximal portion 643 with an outer dimension ($d_2$). The outer dimension ($d_1$) may be greater than the outer dimension ($d_2$) to define a spring abutment surface 646 between the proximal and distal portions 643, 645. In various embodiments, the distal portion 645 of the shaft 641 may include an outer surface with a variety of symmetric or asymmetric edges or angled surfaces (e.g., hexagonal, octagonal, etc.), and the proximal portion 643 of the shaft may include a variety of non-angled or smooth surfaces (e.g., circular, spherical, etc.). One or more pins 644 may extend outward from an outer surface of the shaft 641 along the distal portion 645 (e.g., at or near a proximal end of the distal portion 645).

A spring 150 as the compression resistance element (as discussed above) may be disposed about the proximal portion 643 of the shaft 641. The spring 150 may include an outer dimension ($d_3$) greater than the outer dimension ($d_2$) of the proximal portion 643, but less than the outer dimension ($d_1$) of the distal portion, such that a distal end 154 of the spring 150 slidably contacts or abuts the spring abutment surface 646 along the proximal portion 643.

Figure 6C:
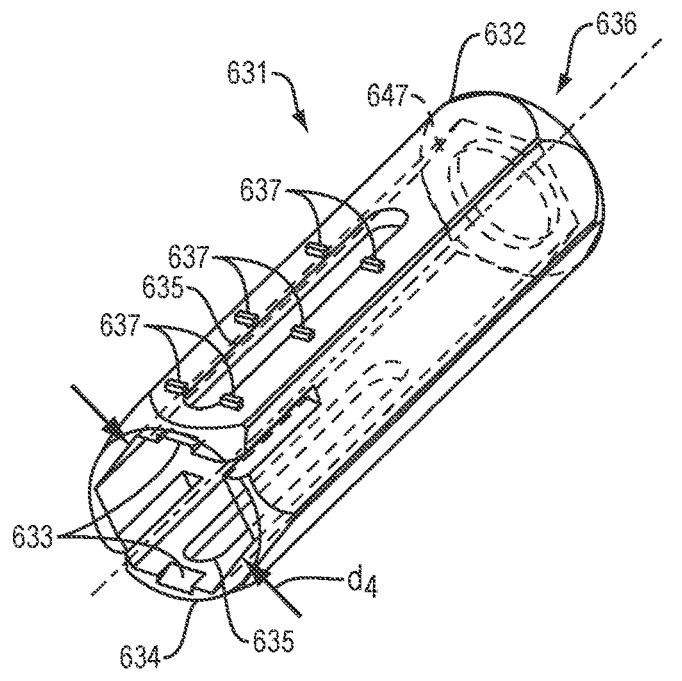

Referring to FIG. 6C, the grip 631 may include a proximal end 632, a distal end 634 and a lumen 636 extending therebetween. The lumen 636 may include an inner dimension ($d_4$) greater than the outer dimension ($d_1$) such that the grip 631 may be slidably disposed over/along at least a portion of the outer surfaces of the proximal and distal portions 643, 645 of the shaft 641, and including the spring 150. In various embodiments, at least a portion of an inner surface of the grip 631 may be configured to match the corresponding outer surface (e.g., hexagonal, octagonal, etc.) of the distal portion 645 of the shaft 641. A spring abutment surface 647 may extend into the lumen 636 at or near the proximal end 632 of the grip 631, e.g., to contact a proximal end 152 of the spring 150 along the proximal portion 643 of the shaft 641 (discussed below). One or more ramped surfaces 633 may extend into the lumen 636 at or near the distal end 634 of the grip 631, and one or more pins slots 635 may extend through a wall of the grip 631 along a longitudinal axis thereof, with the pins slots substantially aligned with the respective ramped surfaces 633. One or more incrementally spaced indicator marks 637 may be disposed on an outer surface of the grip 631 above and/or below the one or more pin slots 635.

Figures 6D, 6E:
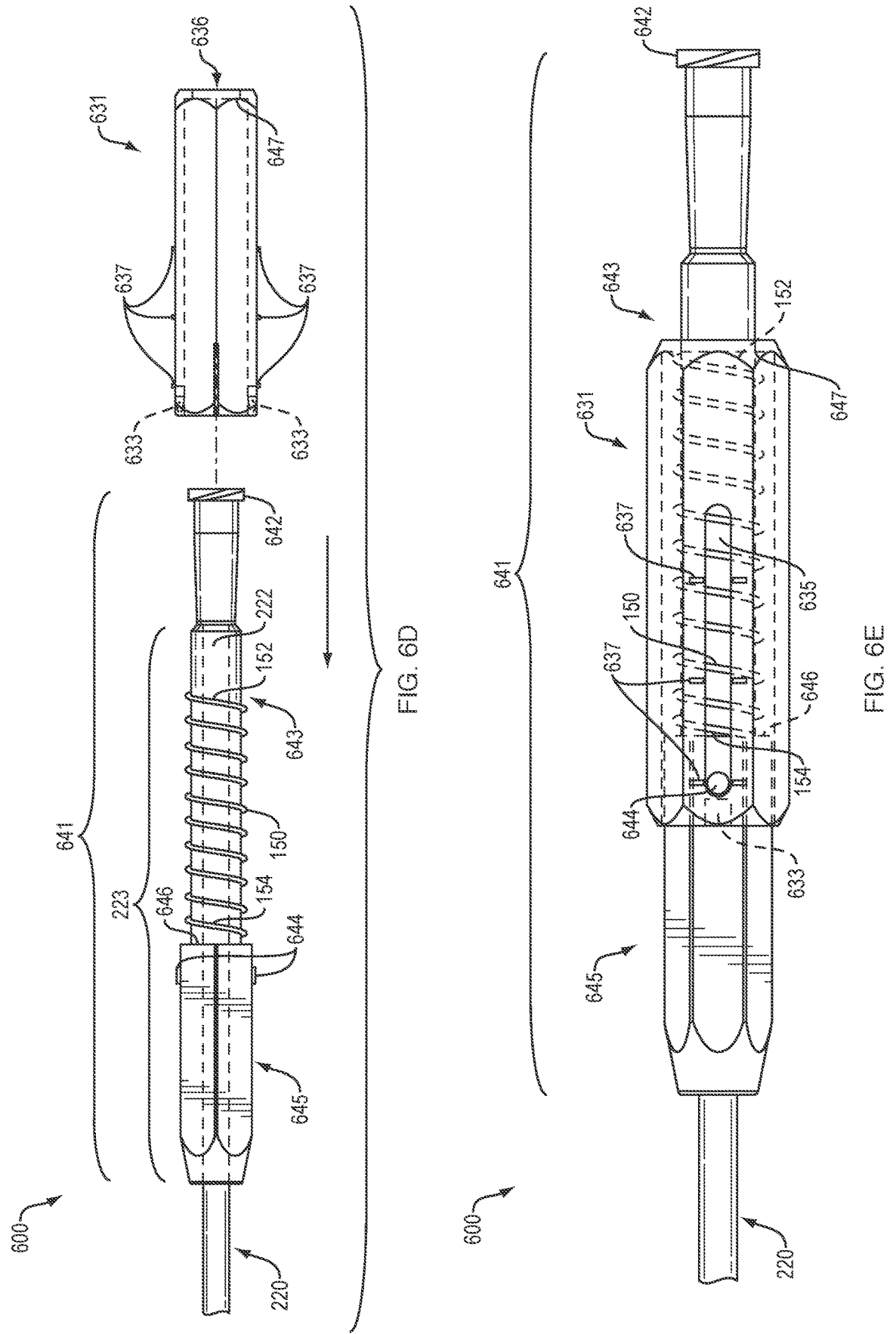

Referring to FIGS. 6D-6E, in one embodiment, the medical device 600 may be assembled by distally advancing the grip 631 over/along the proximal portion 643 of the shaft 641 such that the pins 644 align with and slide over/along the respective ramped surfaces 633. The grip 631 may then be further distally advanced until the pins 644 engage (e.g., extend into) the corresponding pin slots 635. In various embodiments, the female luer connector at the proximal end 642 of the shaft 641 may be configured to receive a corresponding male luer connector (not shown) of a variety of medical devices or instruments, including, for example, imaging catheters, balloon catheters, needles, cannulas and the like. The assembled medical device 600 (e.g., dilator 220 and force gauge 640) may then be used to perform a ureteric calibration procedure, discussed below.

In one embodiment, with the pins 644 aligned with the distal-most indicator mark 637, the distal end 154 of the spring 150 may contact/abut the spring abutment surface 646 of the shaft 641, and the proximal end 152 of the spring 150 may contact/abut the spring abutment surface 647 of the grip 631. In one embodiment, with the pins 644 aligned with the distal-most indicator mark 637, the spring 150 may include a free length ($L_1$), e.g., when in a relaxed configuration, as discussed above.

In use, and by way of example, a medical device 100, 200, 300, 400, 500, 600 of the present disclosure may be introduced into the ureter of a patient over a previously placed guidewire. With the dilator 120, 220 locked to the access sheath 110, 210, 310, 410, 510, a user may hold the grip 131, 231, 331, 431, 531 and distally advance the tapered distal end 124 of the dilator 120 and access sheath into and through the ureter. Similarly, a user may hold the grip 631 and distally advance the tapered distal end 224 of dilator 220 into and through the ureter. For example, in one embodiment, a user may hold the grip in one hand and the access sheath in the other hand to determine the appropriate distal force required to safely advance the access sheath and/or dilator into and through the ureter by tactile feel. Similarly, a user may advance the dilator 220 into and through the ureter by holding the grip 631 between the thumb and forefinger such that the pins 644 remain aligned with the distal-most indicator mark 637, indicating that substantially no resistance beyond a standard amount of "noise" is exerted on the dilator 220. As used herein, "noise" may refer to an acceptable/minimal amount of resistance inherent to flattened or oval-shaped portions of the ureter. For example, in many patients the proximal-most portion of the ureter tends to be flat or collapsed, and may therefore require a threshold level of distal force (e.g., 0.5 pounds) to introduce the distal end of the access sheath and/or dilator. In various embodiments, to minimize or eliminate oscillation within the grip as the access sheath and/or dilator are advanced through the flat portion of the ureter, the spring may be compressed within the lumen of the grip at an initial height less than an equilibrium length $L_1$ at a predetermined initial restoring force greater than the 0.5 pounds, e.g., 1.0 pounds to 2.0 pounds. If the access sheath and/or distal end of the dilator encounter a resistive force due to a restriction or obstruction within the ureter beyond the flat portion, additional distal force (e.g., the force exerted by the user's hand on the grip) may be required to advance the access sheath and/or distal end of the dilator further into the ureter (e.g., past the restriction/obstruction), preferably without causing perforation to the ureter. If the additional distal force required to overcome the resistive force of the restriction/obstruction exceeds the initial restoring force of the spring, the cap, dilator and access sheath may move proximally relative to the grip 531 or cover 631 and compress the spring to a height with a corresponding restoring force equal to the resistive force. With the distal force exerted by the medical device equal to the resistive force, the access sheath and/or dilator may gradually advance past the restriction/obstruction within the ureter. As the resistive force decreases, e.g., the access sheath and/or dilator achieve a "break force" or "release force" and extend distally beyond the restriction/obstruction, the cap, dilator and access sheath may move distally relative to the grip, to increase a height of the spring and decrease the spring's restoring force. A user may visualize the distal force applied by the medical device, which corresponds to the resistive force of the restriction/obstruction, based on a position of the one or more pins relative to the corresponding indicator marks or holes. In various embodiments, the user may evaluate the applied distal force and elect to further increase the distal force to attempt to advance the access sheath further past or through the restriction/obstruction. Alternatively, if the applied distal force approaches or exceeds the user's comfort level (e.g., based on personal experience, tactile feel and/or a reading on the force gauge) the user may elect to withdraw the access sheath from within the ureter and reevaluate the medical approach rather than potentially perforating the ureter.

In various embodiments, an outer surface of the grip 131, 231, 331, 431, 531, 631 and/or cap 140, 240, 340, 440, 540 may include indicator marks and/or indicator numbers which correlate with a predetermined restoring force which cannot be safely exceeded without potentially causing injury to the patient. In various other embodiments, the user may determine an appropriate restoring force using tactile feel. In various other embodiments, a medical device 100, 200, 300, 400, 500, 600 of the present disclosure may be configured to emit an audible tone or vibration within the grip to indicate to a user that a predetermined unsafe restoring force has been exceeded or is being approached. If a user is unable to advance the access sheath 110, 210, 310, 410, 510 and/or tapered distal end 124, 224 of the dilator 120, 220 without exceeding a predetermined restoring force, the medical device may be proximally retracted to withdraw the access sheath from the patient, and an alternative medical procedure performed to resolve the restriction/obstruction before attempting to reinsert the medical device. In various embodiments, the maximum restoring force for safely advancing the access sheath may be determined by interviews and testing with experienced physicians and/or laboratory or animal experiments.

In various embodiments, the indicator numbers and/or indicator marks may represent a variety of incremental restoring forces other than the exemplary ranges provided above. In addition, or alternatively, the number of indicator marks (or indicator numbers), the spacing between the indicator marks (or indicator numbers) and/or the length of the pin slots may be varied depending on the users need to distinguish various incremental increases in restoring force.

The medical devices according to the embodiments described, and in accordance with other embodiments of the present disclosure, alone or in a system or kit or as part of a method or procedure, including with other accessories, may be used in cavities, lumens, tracts, vessels and organs of the body, aside from placing an access sheath within a ureter, such as procedures to drain, access or otherwise treat or diagnose conditions in the peritoneal, abdominal, bronchial or thoracic cavities, vascular vessels, gastrointestinal or urinary tract, uterus, bladder, lung and liver organs, etc.

All of the devices and/or methods disclosed and claimed herein can be made and executed without undue experimentation in light of the present disclosure. While the devices and methods of this disclosure have been described in terms of certain embodiments, it may be apparent to those of skill in the art that variations can be applied to the devices and/or methods and in the steps or in the sequence of steps of the methods described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A method of positioning an access device within a ureter, the method comprising:
   inserting an access device comprising an access sheath, a dilator with an atraumatic distal end, and a force gauge into a ureter of a patient;
   measuring a resistive force when a distal end of the access sheath and/or the dilator encounters an obstruction in the ureter to determine ureteral distensibility prior to performing a ureteroscopy procedure; and
   determining, from the measured resistive force, whether to perform a pre-stenting procedure prior to the ureteroscopy procedure.

2. The method of claim 1, further comprising determining whether the measured resistive force exceeds a pre-determined maximum force.

3. The method of claim 2, further comprising determining the pre-determined maximum force by tactile feel, an audible alarm, a visual alarm, or an indicator mark on the access device.

4. The method of claim 1, further comprising distally advancing the access sheath and dilator beyond the obstruction if the measured resistive force is less than or equal to a pre-determined maximum force.

5. The method of claim 1, further comprising proximally retracting the access sheath and dilator from within the ureter if the measured resistive force exceeds a pre-determined maximum force.

6. A method of positioning a medical device capable of monitoring forces applied by the medical device within a patient's body, said method comprising:
   inserting an access device into a body passage within a patient, the access device having an indicator, an access sheath defining a lumen therethrough, an elongate member disposed within the lumen of the access sheath and having a distal end, and a force gauge disposed on the access sheath;
   correlating and indicating on the indicator an amount of resistive force exerted on the access sheath and/or the elongate member upon the access sheath and/or the elongate member contacting, without passing through, an obstruction within the body passage; and
   determining, from the amount of resistive force exerted on the access sheath and indicated on the indicator, whether to perform a secondary procedure.

7. The method of claim 6, further comprising indicating a restoring force of a spring of the force gauge upon the access sheath and/or elongate element contacting, without passing through, an obstruction within the body passage.

8. The method of claim 7, wherein the spring is positioned within a grip of the force gauge, said method further comprising moving the grip of the force gauge relative to cap of the force gauge to cause indicators of the force gauge to indicate the resistive force of the spring.

9. The method of claim 6 further comprising determining whether the amount of resistive force exceeds a pre-determined maximum force.

10. The method of claim 9, further comprising determining the pre-determined maximum force by tactile feel, an audible alarm, a visual alarm, or an indicator mark on the access device.

11. The method of claim 6, further comprising distally advancing the access sheath and elongate element beyond the obstruction if the amount of resistive force is less than or equal to a pre-determined maximum force.

12. The method of claim 6, further comprising proximally retracting the access sheath and elongate element from within the body passage if the amount of resistive force exceeds a pre-determined maximum force.

13. A method of monitoring forces applied by a medical device within a patient's body, said method comprising:

inserting an access sheath, defining a lumen therethrough, into the patient's body, with an elongate element disposed within the lumen of the access sheath, the elongate element having a distal end tapered to facilitate atraumatic advancement through a body passage; and measuring, on a force gauge disposed on the access sheath, a resistive force on the access sheath and/or elongate element upon contacting, without passing through, an obstruction within the body passage; and determining whether to perform a secondary procedure in response to the measured resistive force on the access sheath and/or the elongated element, wherein when the measured resistive force exceeds a pre-determined maximum force, then performing the secondary procedure.

14. The method of claim 13, further comprising measuring a restoring force of a spring of the force gauge upon the access sheath and/or dilator contacting, without passing through, an obstruction within the body passage.

15. The method of claim 14, further comprising moving a grip of the force gauge relative to a cap of the force gauge to change a height of the spring within the grip.

16. The method of claim 13, further comprising determining whether the measured resistive force exceeds a pre-determined maximum force.

17. The method of claim 16, further comprising determining the pre-determined maximum force by tactile feel, an audible alarm, a visual alarm, or an indicator mark on the access device.

18. The method of claim 13, further comprising distally advancing the access sheath and dilator beyond the obstruction if the measured resistive force is less than or equal to a pre-determined maximum force.

19. The medical device of claim 13, further comprising proximally retracting the access sheath and dilator from within the body passage if the measured resistive force exceeds a pre-determined maximum force.

* * * * *